United States Patent
Neumann

(10) Patent No.: US 11,139,063 B1
(45) Date of Patent: Oct. 5, 2021

(54) SYSTEMS AND METHODS FOR GENERATING A MICROBIOME BALANCE PLAN FOR PREVENTION OF BACTERIAL INFECTION

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/136,126

(22) Filed: Dec. 29, 2020

(51) Int. Cl.
| | |
|---|---|
| *G16H 20/60* | (2018.01) |
| *G16H 10/60* | (2018.01) |
| *G06N 20/00* | (2019.01) |
| *G16H 70/60* | (2018.01) |
| *G16H 50/70* | (2018.01) |
| *G16H 50/20* | (2018.01) |

(52) U.S. Cl.
CPC .............. *G16H 20/60* (2018.01); *G06N 20/00* (2019.01); *G16H 10/60* (2018.01); *G16H 50/20* (2018.01); *G16H 50/70* (2018.01); *G16H 70/60* (2018.01)

(58) Field of Classification Search
CPC ........ G16H 20/60; G16H 70/60; G16H 10/60; G16H 50/70; G16H 50/20; G06N 20/00
USPC .......................................................... 705/2–3
See application file for complete search history.

(56) References Cited

U.S. PATENT DOCUMENTS

| | | | |
|---|---|---|---|
| 7,349,808 B1* | 3/2008 | Kreiswirth | G16H 70/60 702/19 |
| 10,265,009 B2* | 4/2019 | Apte | A61B 5/4836 |
| 10,357,157 B2 | 7/2019 | Apte | |

(Continued)

FOREIGN PATENT DOCUMENTS

WO     2020201457     10/2020

OTHER PUBLICATIONS

Title: Dietary Quercetin Increases Colonic Microbial Diversity and Attenuates Colitis Severity in Citrobacter rodentium-Infected Mice; by: Lin; Date: May 16, 2019

(Continued)

*Primary Examiner* — Michael Tomaszewski
(74) *Attorney, Agent, or Firm* — Caldwell Intellectual Property Law, LLC

(57) ABSTRACT

A system for generating a microbiome balance plan including a computing device configured to receive at least a microbe indicator, retrieve a microbiome profile, assign the microbiome profile to a microbe category, determine, using the microbe category and the microbiome profile, a microbe reduction strategy, determining at least a first nutrient amount that aids in reduction of at least a first microbe, identify a first nutrition element, wherein the first nutrition element contains at least a first nutrient amount, determine, using the microbe category and the microbiome profile, a microbiome supplementation program, identifying at least a second microbe to be included to the microbiome profile, determining at least a second nutrition element that aids in supplementation of the at least a second microbe, identify a second plurality of nutrition elements, generate a microbiome balance plan, using the microbe reduction strategy and the microbiome supplementation program.

18 Claims, 8 Drawing Sheets

(56) References Cited

U.S. PATENT DOCUMENTS

| | | | |
|---|---|---|---|
| 2002/0107641 A1* | 8/2002 | Schaeffer | G06Q 30/02 |
| | | | 702/19 |
| 2002/0120408 A1* | 8/2002 | Kreiswirth | G16H 10/60 |
| | | | 702/20 |
| 2010/0280837 A1* | 11/2010 | Naidich | G16H 10/60 |
| | | | 705/2 |
| 2012/0276059 A1 | 11/2012 | Boone | |
| 2015/0057574 A1* | 2/2015 | Baym | G16H 10/60 |
| | | | 600/570 |
| 2015/0058368 A1* | 2/2015 | Hyde | G16H 20/13 |
| | | | 707/756 |
| 2015/0072338 A1* | 3/2015 | Holmes | G01N 33/56944 |
| | | | 435/5 |
| 2016/0040216 A1* | 2/2016 | Akins | C12Q 1/689 |
| | | | 506/9 |
| 2017/0159108 A1 | 6/2017 | Budding | |
| 2019/0252058 A1 | 8/2019 | Wolf | |
| 2019/0267140 A1 | 8/2019 | Segal | |
| 2020/0013488 A1 | 1/2020 | Lui | |
| 2020/0277658 A1 | 9/2020 | Cutcliffe | |
| 2020/0286623 A1 | 9/2020 | Apte | |
| 2020/0308627 A1 | 10/2020 | Jain | |

OTHER PUBLICATIONS https://gut.bmj.com/content/69/8/1520?int_source=trendmd&int_medium=cpc&int_campaign=usage-042019; Title: Big data in IBD: big progress for clinical practice; Date: Jul. 7, 2020; by: Tabib, Nasim Sadat Seyed.

https://www.nature.com/articles/srep35216; Title: The fecal microbiota as a biomarker for disease activity in Crohn's disease; Date: Oct. 13, 2016; by: Tedjo, Danyta I.

https://www.mdpi.com/2072-6643/7/2/1282; Title: Pilot dietary intervention with heat-stabilized rice bran modulates stool microbiota and metabolites in healthy adults; Date: Feb. 16, 2015; by: Sheflin, Amy M.

https://www.ncbi.nlm.nih.gov/pmc/articles/PMC4299332/; Title: Application of metagenomics in the human gut microbiome; Date: Jan. 21, 2015; by: Wang, Wei-Lin.

* cited by examiner

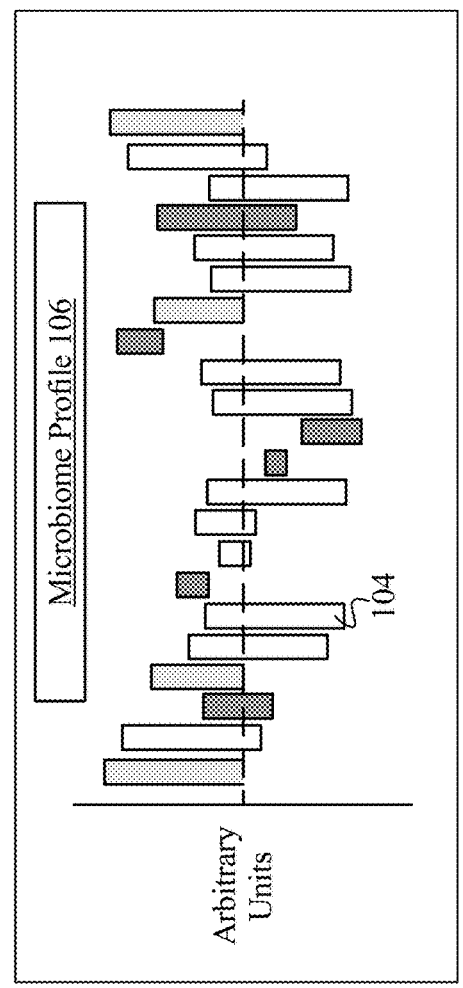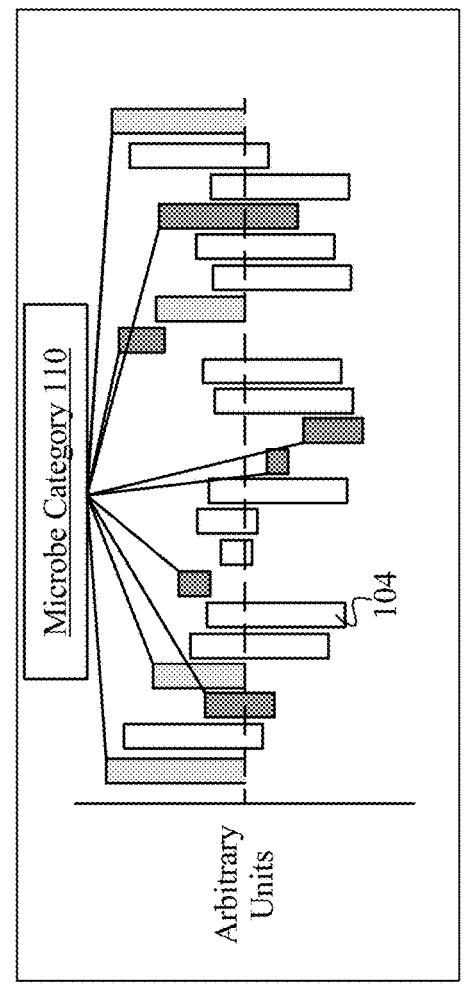

US 11,139,063 B1

SYSTEMS AND METHODS FOR GENERATING A MICROBIOME BALANCE PLAN FOR PREVENTION OF BACTERIAL INFECTION

FIELD OF THE INVENTION

The present invention generally relates to the field of nutrient planning for bacterial infection. In particular, the present invention is directed to systems and methods for generating a microbiome balance plan for prevention of bacterial infection.

BACKGROUND

Addressing bacterial infection is typically focused on diagnostic procedures based on culturing techniques, or cell-based assays for detecting the presence of spores (e.g. potassium hydroxide for fungal spores), lipopolysaccharide (LPS antigen), bacterial cells (e.g. selective and differential media), and other organismal bodies (e.g. flagella, toxins, and the like). There exist difficulties in controlling infectious disease by modulating the populations of microorganisms that coexist among the ecosystem of the human body.

SUMMARY OF THE DISCLOSURE

In an aspect, a system for generating a microbiome balance plan for prevention of bacterial infection including a computing device configured to receive at least a microbe indicator, wherein a microbe indicator is a biomarker that originates from a user, retrieve a microbiome profile related to the user, assign the microbiome profile to a microbe category, determine, using the microbe category and the microbiome profile, a microbe reduction strategy, wherein determining the microbe reduction strategy includes locating at least a first microbe to be reduced from the microbiome profile, identifying at least a first nutrient amount that aids in reduction of the at least a first microbe, and determining at least a first nutrition element, wherein the at least a first nutrition element includes the at least a first nutrient, identify, using the microbe category and the microbiome profile, a microbiome supplementation program, wherein determining the microbiome supplementation program includes locating at least a second microbe to be included to the microbiome profile, determining at least a second nutrient amount that aids in supplementation to microbiome profile of the at least a second microbe, and identifying at least a second nutrition element, wherein of the at least a second nutrition element includes the at least a second nutrient amount, and generate a microbiome balance plan, using the microbe reduction strategy and the microbiome supplementation program, wherein the microbiome balance plan includes a frequency a magnitude of the at least a first nutrient element and a frequency and a magnitude of the at least a second nutrient element.

In another aspect, a method for generating a microbiome balance plan for prevention of bacterial infection, including receiving, by a computing device, at least a microbe indicator, wherein a microbe indicator is a biomarker that originates from a user, retrieving, by the computing device, a microbiome profile related to the user, assigning, by the computing device, the microbiome profile to a microbe category, determining, by the computing device, using the microbe category and the microbiome profile, a microbe reduction strategy, wherein determining the microbe reduction strategy includes locating at least a first microbe to be reduced from the microbiome profile, identifying at least a first nutrient amount that aids in reduction of the at least a first microbe, and determining at least a first nutrition element, wherein the at least a first nutrition element includes the at least a first nutrient, identifying, by the computing device, using the microbe category and the microbiome profile, a microbiome supplementation program, wherein determining the microbiome supplementation program includes locating at least a second microbe to be included to the microbiome profile, determining at least a second nutrient amount that aids in supplementation to microbiome profile of the at least a second microbe, and identifying at least a second nutrition element, wherein of the at least a second nutrition element includes the at least a second nutrient amount, and generating, by the computing device, a microbiome balance plan, using the microbe reduction strategy and the microbiome supplementation program, wherein the microbiome balance plan includes a frequency a magnitude of the at least a first nutrient element and a frequency and a magnitude of the at least a second nutrient element.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A and 4B are a diagrammatic representation of a microbiome profile;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a microbiome balance plan for prevention of bacterial infection. In an embodiment, computing device is configured to receive bacterial indicators and retrieve a microbiome profile. Computing device may classify microbiome profile of a user microbe categories according to locating pathogens for reduction and microbes missing from the proper microbiome balance. Computing device may employ machine-learning to derive models to automatedly locate microbes that may increase infection risk and/or locate microbes that are absent but present among a cohort of other users. Computing device may derive appropriate nutrient amounts that support colonization of the correct balance of microbes as part of user microbiome, wherein the correct balance works toward preventing infection of pathogens and fostering beneficial microbiota.

Figure 1:
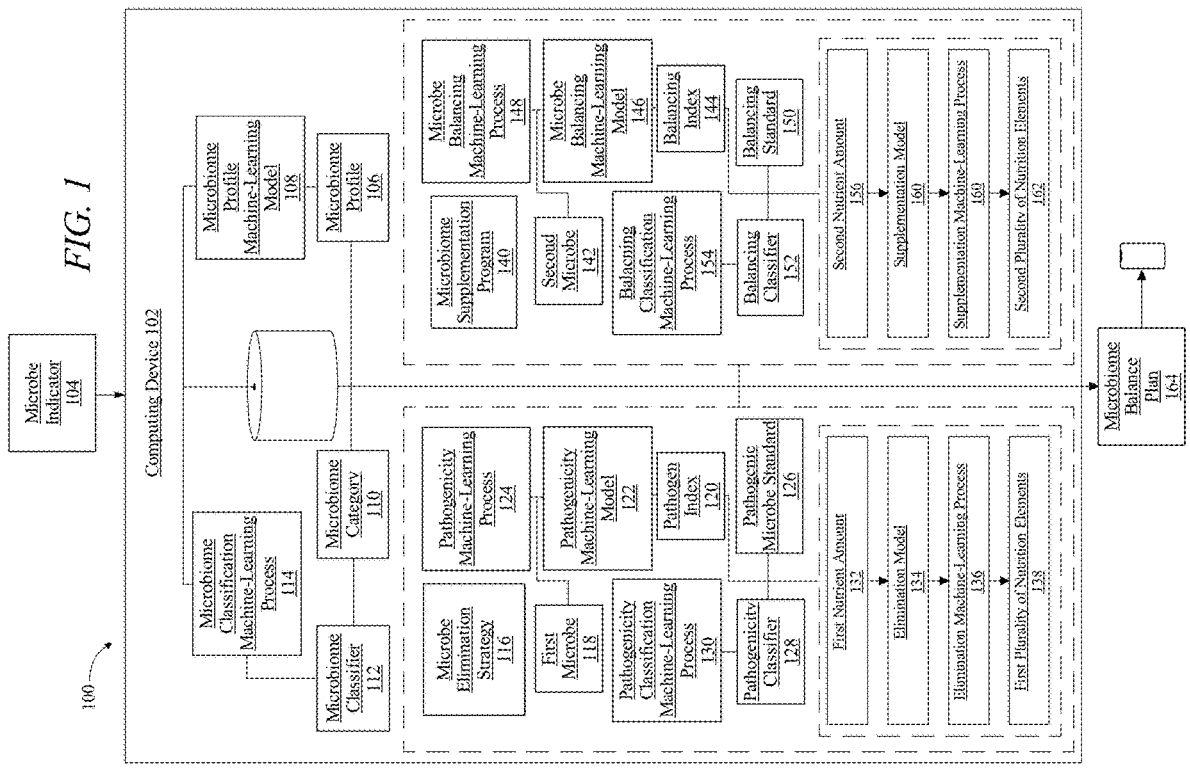
FIG. 1 is a block diagram illustrating a system for generating a microbiome balance plan for prevention of bacterial infection.

Referring now to FIG. 1, an exemplary embodiment of a system 100 for generating a microbiome balance plan for prevention of bacterial infection is illustrated. System includes a computing device 102. Computing device 102 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 102 may include a single computing device operating independently, or may include two or more computing device operating in concert, in parallel, sequentially or the like; two or more computing devices may be included together in a single computing device or in two or more computing devices. Computing device 102 may interface or communicate with one or more additional devices as described below in further detail via a network interface device. Network interface device may be utilized for connecting computing device 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software and the like) may be communicated to and/or from a computer and/or a computing device. Computing device 102 may include but is not limited to, for example, a computing device or cluster of computing devices in a first location and a second computing device or cluster of computing devices in a second location. Computing device 102 may include one or more computing devices dedicated to data storage, security, distribution of traffic for load balancing, and the like. Computing device 102 may distribute one or more computing tasks as described below across a plurality of computing devices of computing device, which may operate in parallel, in series, redundantly, or in any other manner used for distribution of tasks or memory between computing devices. Computing device 102 may be implemented using a "shared nothing" architecture in which data is cached at the worker, in an embodiment, this may enable scalability of system 100 and/or computing device.

With continued reference to FIG. 1, computing device 102 may be designed and/or configured to perform any method, method step, or sequence of method steps in any embodiment described in this disclosure, in any order and with any degree of repetition. For instance, computing device 102 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 102 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a microbe indicator. A "microbe indicator," as used in this disclosure, is a biological and/or chemical substance or process that is indicative of a relationship between the microbiome and the body. A "microbiome," as used in this disclosure, is a heterogeneous or homogenous aggregate of microorganisms and their associated products that reside on or within a user. A "microorganism," as used in this disclosure, is a microscopic non-human organism. A microorganism may include a bacterium, archaea, fungi, protist, virus, amoeba, parasite, spore, egg, larvae, and the like, that may reside in within or on a body. A microorganism may be simply referred to as a "microbe". Microorganisms may include microbes with populations supported in and/or colonizing biofluids, tissues, on the skin, epithelia of organs, cavities of the body, and the like. For instance and without limitation, the human microbiome may include microorganisms that reside on or within the skin, mammary glands, placenta, seminal fluid, uterus, ovarian follicles, lung, saliva, oral mucosa, conjunctiva, biliary tract, and gastrointestinal tract. Human microbiome may include colonization by many microorganisms; it is estimated is that the average human body is inhabited by ten times as many non-human cells as human cells, some studies estimate that ratio as 3:1, or even 1:1. Some microorganisms that colonize humans are commensal, meaning they may co-exist without harm; others have a mutualistic relationship with their hosts, such as a metabolic symbiosis where microbes improve digestion, whereas the host provides a niche. Conversely, some non-pathogenic microorganisms may harm human hosts via the metabolites they produce, like trimethylamine, which the human body converts to trimethylamine N-oxide via FMO3-mediated oxidation. Microbes that are expected to be present, and that under normal circumstances do not cause disease, may be deemed 'normal flora' or 'normal microbiota'.

Continuing in reference to FIG. 1, microbiome indicator 108 may include analysis of molecules from a biological extraction of a user. A biological extraction may include an analysis of a physical example of a user, such as a stool sample, DNA sequencing, and the like Microbe indicator 104 may include measurements of the presence of microorganisms, such as culturing results relating to microorganisms (bacteria culturing, viral plaque assays, and the like). Microbe indicator 104 may include diagnostic results such as Enterotube™ II results, metabolic profiling, genetic sequence (e.g. using targeted PCR probe-based microbiome profiling), biochip and/or sensor-based microbiome profiling (e.g. immobilizing macromolecules to a microarray, and the like). Receiving the at least a microbe indicator 104 may include receiving a result of one or more tests relating to the user and/or analysis of one or more tests. For instance and without limitation, an analysis of a biological extraction such as a blood panel test, lipid panel, genomic sequencing, and the like. Such data may be received and/or identified as a biological extraction of a user, which may include analysis of a physical sample of a user such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, microbe indicator 104 may include test results of screening and/or early detection of infection, diagnostic procedures, prognostic indicators from other diagnoses, from predictors identified in a medical history, and information relating to biomolecules associated with the user such as the presence of and/or concentrations of: BBA68, BBA64, BBA74, BBK32, VisEC6, BBA15, BBB19, BB032, BBA24, BB0147, CRP, IL-6, PCT, Serum Amyloid A (SAA), ESR, sTREM-1, ANP, PSP, IL-8, IL-27, suPAR, and the like. Microbe indicator 104 may include diagnostics, for instance the use of a K-OH (potassium hydroxide) test for the presence of fungal spores, catalase test, coagulase test, microscopy methods (e.g. wet mounts, Gram staining, and the like), ELISA tests, antigen-antibody tests, and the like Continuing in reference to FIG. 1, microbe indicator 104 may include DNA sequencing data. For instance, sequencing of 16S ribosomal RNA (rRNA) among microbial species. Such data may include "next-gen", or "second-generation" sequencing technologies with incomplete and variable sequences obtained, for instance, from stool samples. There exist a multitude of nucleic acid primer sequences used for determining the presence of microbiota species, with individual species resolution, and 1,000's+ organismal throughout. Such primers may include DNA primers for reverse-transcription PCR (rtPCR) to generate cDNA libraries from RNA templates. In such an example, microbe indicator 104 may include the RNA sample and its analysis by rtPCR. Microbe indicator 104 may include any PCR experimentation analysis (e.g. qPCR, RT-qPCR, host start PCR, and the like) that may be used to amplify microorganism nucleic acid and detect the presence of and identify microorganisms. Microbe indicator 104 may include data relating to the presence and/or concentration of products relating from a microorganism (e.g. toxins, metabolic waste products, LPS, and the like). Microbe indicator 104 may include data relating to the presence and/or concentration of products relating from infection by a microorganism (e.g. blood serum proteins, complement, antibodies, T-cell activation, and the like).

Continuing in reference to FIG. 1, microbe indicator 104 may include culturing techniques used to support growth of a population of microorganisms isolated from a user to identify and measure the population size of microorganism. Microbe indicator 104 may include analysis of growth on selective media (e.g. to select for the presence of a microorganism such as EMB, MacConkey, and the like), differential media (e.g. to distinguish between species, such as blood agar, chocolate agar, and the like), Kirby-Bauer antibiotic sensitivity test, among other assays regarding growth, isolation, and characterization of microorganisms originating from a user. Microbe indicator 104 may include biochemical analysis of microbial products such as the presence of bacterial spores such as *bacillus* spp. spores in the gut.

Continuing in reference to FIG. 1, microbe indicator 104 may include results enumerating the identification of mutations in nucleic acid sequences. Microbe indicator 104 may include the presents of single nucleotide polymorphisms (SNPs) in genetic sequences. Microbe indicator 104 may include epigenetic factors, such as non-heritable alterations to genetic information. Microbe indicator 104 may include genetic and epigenetic factors for the user, for instance as a user may have mutations and/or SNPs in lactate dehydrogenase, or its gene/enzyme regulation, as it relates to symptomology relating to lactose intolerance. Microbe indicator 104 may include genetic and epigenetic factors for microbes originating from a user, for instance the presence of mutations regarding to antibiotic-resistance (e.g. inheriting R-factors, mutation in 30S/50S rRNA leading to rifampicin resistance, and the like).

Continuing in reference to FIG. 1, computing device 102 may receive microbe indicator 104 as user input. User input may be received via a "graphical user interface," which as used is this disclosure, is a form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction such as replying to health state questionnaire for symptomology onboarding, uploading a genetic sequencing file, hyperlinking a medical history document, and the like) with a user device. A person skilled in the art, having the benefit of the entirety of this disclosure, will be aware of various additional test data, biomarker data, analysis, and the like, that may be received as microbe indicator data and how system may receive such data as input.

Continuing in reference to FIG. 1, microbe indicator 104 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, microbe indicator 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module, as described in further detail below, to produce outputs given data provided as inputs; this is in contrast to a non-machine learning software programing where the commands to be executed are determined in advance by a subject and written in a programming language.

Continuing in reference to FIG. 1, microbe indicator 104 may be organized into training data sets and stored and/or retrieved by computing device 102, without limitation, as a relational database, a key-value retrieval database such as a NOSQL database, or any other format or structure for use as a database that a person skilled in the art may recognize as suitable upon review of the entirety of this disclosure. Microbe indicator 104 training data may alternatively or additionally be implemented using a distributed data storage protocol and/or data structure, such as a distributed hash table and the like. Microbe indicator 104 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of microbe indicators may be stored, retrieved, organized, and/or reflect data and/or records as used herein, as well as categories and/or populations of data consistent with this disclosure.

Continuing in reference to FIG. 1, computing device 102 is configured to retrieve a microbiome profile related to the user. A "microbiome profile," as used in this disclosure, is a profile that includes at least a metric relating to a plurality of microbes as a function of the at least a microbe indicator 104. Microbiome profile 106 may include any number of current microbial colonization state determinations including 'past infections', 'vaccinations', 'antibiotics taken', 'surgeries' (e.g. appendectomy, adenoidectomy, and the like), and the like. Microbiome profile 106 may include the identification of microorganism family, genus, species, strain, serotypes, and the like. Microbiome profile 106 may include data represented by strings, numerical values, mathematical expressions, functions, matrices, vectors, and the like. Microbiome profile 106 may include a plurality of metrics and their relationships to a plurality of microbes as a function of the at least a microbe indicator 104, such as the presence of and degree of colonization of bacteria isolates.

Continuing in reference to FIG. 1, microbiome profile 106 may include qualitative determinations, such as binary "yes"/"no" determinations for harboring a bacterial species, pathogen, antibiotic resistant strain, "normal"/"abnormal" determinations about the presence of and/or concentration of microbe indicators 104, for instance as compared to a normalized threshold value of a biomarker among a subset of healthy adults. Microbiome profile 106 may include mathematical representations of the current state of the microbiome and bacterial infection, such as a function describing, for instance, the risk of developing infection as a function of time. Such representations of microbiome profile 106 may allow for determinations such as instantaneous infection risk, such as daily, weekly, monthly, and the like, risks.

Continuing in reference to FIG. 1, retrieving microbiome profile 106 may include a process of searching for, locating, and returning microbiome profile 106 data. For example, microbiome profile 106 may be retrieved as documentation on a computer to be viewed or modified such as files in a directory, database, and the like. In non-limiting illustrative embodiments, computing device 102 may locate and download microbiome profile 106 via a web browser and the Internet, receive as input via a software application and a user device, and the like Still referring to FIG. 1, computing device 104 may retrieve microbiome profile 106 from a database. Database may be implemented, without limitation, as a relational database, a key-value retrieval database such as a NOSQL database, or any other format or structure for use as a database that a person skilled in the art would, upon the benefit of this disclosure in its entirety, may recognize as suitable upon review of the entirety of this disclosure. Database may include a microbiome database, as described in further detail below. Alternatively or additionally, database may be implemented using a distributed data storage protocol and/or data structure, such as a distributed hash table and the like. Database may include a plurality of data entries and/or records, as described herein. Data entries for microbe profile 106 may be flagged with or linked to one or more additional elements of information, which may be reflected in data entry cells and/or in linked tables such as tables related by one or more indices in a relational database.

Continuing in reference to FIG. 1, retrieving microbiome profile 106 may include training a microbiome profile machine-learning model with training data that includes a plurality of data entries wherein each entry correlates microbe indicators 104 to a plurality of microorganisms and generating the microbiome profile 106 as a function of the microbiome profile machine-learning model and the at least a microbe indicator 104. Correlating microbial indicators 108 to a plurality of microorganisms may include deriving relationships between microbe indicator(s) 104 as they relate to the identification of and or quantification of microorganism populations in the user. Such a process may include threshold values, for instance biomarker cutoffs for determining that a user may be harboring a microorganism, for comparing microbe indicator 104. Such training data may include data such as cytokine levels, genes expression levels, white blood cell levels, and metabolites correlated to microorganism identities according to what the levels may be, combinations of levels, level cutoffs, and the like.

Continuing in reference to FIG. 1, microbiome profile machine-learning model 108 may include any machine-learning algorithm such as K-nearest neighbors algorithm, a lazy naïve Bayes algorithm, and the like, any machine-learning process such as supervised machine-learning, unsupervised machine-learning, or the like, or any machine-learning method such as neural nets, deep learning, and the like, as described in further detail below. Microbiome profile machine-learning model 108 may be trained to derive an algorithm, function, series of equations, or any mathematical operation, relationship, or heuristic, that can automatedly accept an input of microbe indicator(s) 108 and assign a numerical value to and generate an output of microbiome profile 106. Microbiome profile machine-learning model 108 may derive individual functions describing unique relationships observed from the training data for each microbe indicator 104, wherein different relationships may emerge between users and user cohorts such as subsets of alike users, healthy users, obese users, 18-25 yrs. old, among others. Computing device 102 may generate the microbiome profile 106 as a function of the microbiome profile machine-learning model 108 and the at least a microbe indicator 104 (input). Microbiome profile 106 include any number of parameters.

Continuing in reference to FIG. 1, training data for microbiome profile machine-learning model 108 may include results from biological extraction samples, health state questionnaires regarding symptomology, medical histories, physician assessments, lab work, and the like. Microbiome profile training data may originate from the subject, for instance via a questionnaire and a user interface with computing device 102 to provide medical history data, nutritional input, food intolerances, and the like Computing device 102 may receive training data for training microbiome profile machine-learning model 108. Receiving such training data may include receiving whole genome sequencing, gene expression patterns, and the like, for instance as provided by a genomic sequencing entity, hospital, database, the Internet, and the like Microbiome profile training data may include raw data values recorded and transmitted to computing device 102 via a wearable device such as a bioimpedance device, ECG/EKG/EEG monitor, physiological sensors, blood pressure monitor, blood sugar and volatile organic compound (VOC) monitor, and the like. Microbiome profile training data may originate from an individual other than user, including for instance a physician, lab technician, nurse, caretaker, and the like. It is important to note that training data for machine-learning processes, algorithms, and/or models used herein may originate from any source described for microbiome profile training data.

Continuing in reference to FIG. 1, in non-limiting illustrative examples, the expression levels of a variety of isolates from human stool samples such as bacterial species identifications, sequencing data, and the like, which may be retrieved from a database, such as a repository of peer-reviewed research (e.g. National Center for Biotechnology Information as part of the United States National Library of Medicine), and the trained microbiome profile machine-learning model 108 derived function(s) may calculate an average and statistical evaluation (mean±S.D.) from the data, across which the user's microbe indicators 104 are compared. In such an example, microbiome profile machine-learning model 108 may derive a scoring function that includes a relationship for how to arrive at a solution according to the user's microbe indicator (e.g. number of mRNA transcripts presence in stool) as it relates to the presence of a microorganism. In this way, computing device 102 may use the trained microbiome profile machine-learning model 108 to "learn" how identify and enumerate all microorganisms that may relate to the user. Microbiome profile 106 may become increasingly more complete, and more robust, with larger sets of microbe indicators 104.

Continuing in reference to FIG. 1, computing device 102 is configured to assign the microbiome profile 106 to a microbe category. A "microbe category," as used in this disclosure, is a determination about a current microbial colonization state of the user according to a classification of the user as a function of a subset of users. Microbe category 110 may include tissue or organ type classification, such as "skin infection", "gum infection", and the like Microbe category 110 may include a microorganism species, identifier, or groping such as "*enterococcus*", "*Clostridium* spp." and the like Microbe category 110 may include a designation about antibiotic resistance, such as "MRSA" (methicillin-resistant *Staph aureus*), "VREs" (vancomycin-resistant *enterococcus*), and the like Microbe category 110 may include a designation regarding a type of bodily dysfunction that may involve a particular microorganism, or lack thereof, "dairy intolerance", "celiac disease", "puffy adenoids", "allergic reaction", and the like Microbe category 110 may include a predictive classification, where a user does not currently have a bacterial infection but may include data that indicates a microbe category 110 with which the user may be most closely categorized to, such as for 'imminent infection'. For instance, a medical history of ear infections may classify an individual into categorizations concerning microorganisms that cause middle ear infections, such as "*Streptococcus pneumoniae* (pneumococcus)", "Hemophilus influenzae", "Pseudomonas", "Moraxella", and the like, microbe category 110, despite not currently having ear infection. Microbiome profile 106 may have associated with it an identifier, such as a label, that corresponds to a microbe category 110, series of microorganism identities, and the like Continuing in reference to FIG. 1, assigning microbiome profile 106 to microbe category 110 may include training a microbiome classifier using a microbiome classification machine-learning process and training data which includes a plurality of data entries of microbiome profile data from subsets of categorized users. Microbiome classification machine-learning process may generate microbiome classifier using training data. Training data may include bacterial species, microbe biomarkers 108, and the like, correlated to data entries that may be recognized as microbe categories 120. Training data may originate from any source as described above. A "microbiome classifier" may include a machine-learning model, such as a mathematical model, neural net, or program generated by a machine learning algorithm known as a "classification algorithm," as described in further detail below. Microbiome classifier 112 may sort inputs (such as the data in the microbiome profile 106) into categories or bins of data (such as classifying the data into a microbe category 110), outputting the bins of data and/or labels associated therewith. In non-limiting illustrative examples, training data used for such a classifier may include a set of microbe indicators 104 as it relates to classes of bacterial infections, symptoms, bacterial species, and the like. For instance, training data may include ranges of user biological extraction values as they may relate to the variety of infections.

Continuing in reference to FIG. 1, microbiome classification machine-learning process 114 may include any classification machine-learning algorithm which may be performed by machine-learning module, as described in further detail below. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a microbiome classifier may classify elements of training data to elements that characterizes a sub-population, such as a subset of microbe indicator 104 (e.g. bacterial isolates as it relates to a variety of microbiome categories 120) and/or other analyzed items and/or phenomena for which a subset of training data may be selected. In this way, microbiome classifier Continuing in reference to FIG. 1, computing device may classify the microbiome profile 106 to the microbe category 110 using the microbiome classifier 112 and assigning the microbe category 110 as a function of the classifying. For instance and without limitation, training data may include sets of microbe indicators 104 correlated to bacterial infection types, species, tissues, and the like, as described above. Microbiome classification machine-learning process 114 may be trained with training data to "learn" how to categorize a user's microbiome profile 106 as a function of trends gene expression, SNPs, bacterial isolates, user symptomology, and the like. Such training data may originate from a variety of sources, for instance from user input via a health state questionnaire and a graphical user interface. Training data may originate from a biological extraction test result such as genetic sequencing from user stool samples, blood panel for metabolites, and the like Training data may originate from a user's medical history, a wearable device, a family history of disease, and the like. Training data may similarly originate from any source, as described above, for microbe indicator 104 and determining microbiome profile 106. In this way, microbe classifier 124 may be free to "learn" how to generate new microbe categories 120 derived from relationships observed in training data.

Continuing in reference to FIG. 1, classification using microbiome classifier 112 may include identifying which set of categories (microbe category 110) an observation (microbiome profile 106) belongs. Classification may include clustering based on pattern recognition, wherein the presence of microbe indicators 104, such as bacterial species, genetic indicators, symptoms, and the like, identified in microbiome profile 106 relate to a particular microbe category 110. Such classification methods may include binary classification, where the microbiome profile 106 is simply matched to each existing microbe category 110 and sorted into a category based on a "yes"/"no" match. Classification may include weighting, scoring, or otherwise assigning a numerical valuation to data elements in microbiome profile 106 as it relates to each microbe category 110. Such a score may represent a likelihood, probability, or other statistical identifier that relates to the classification into microbe category 110, where the highest score may be selected depending on the definition of "highest".

Continuing in reference to FIG. 1, computing device 102 is configured to determine, using the microbe category 110 and the microbiome profile 106, a microbe reduction strategy. A "microbe reduction strategy," as used in this disclosure, is a strategy including at least a nutrient amount intended to be taken by the user to reduce the population of a microorganism. A "nutrient amount," as used in this disclosure, is a numerical value(s) relating to the amount of a nutrient. A "nutrient," as used in this disclosure, is any biologically active compound whose consumption is intended to have an effect on the microbiome. Reducing the population of a microorganism may include slowing the growth rate, undoing colonization, depleting the population, suppressing growth by supporting competing microorganisms, among other strategies.

Continuing in reference to FIG. 1, determining a microbe reduction strategy 116 includes identifying at least a first microbe 118 to be eliminated from microbiome profile 106, wherein identifying at least a first microbe 118 may include generating a pathogen index. A "first microbe," as used in this disclosure, is at least one microorganism, microorganism type, or the like, that was identified to be removed from microbiome profile 106. A "pathogen index," as used in this disclosure, is a systematic index used to classify a microorganism as a pathogen. Pathogen index 120 may include a scoring index, repository, listing, and the like, of microbes (bacteria, protists, yeasts, and the like) that represent pathogens for user. Pathogens may be user-specific (one isolate may represent a pathogen for a particular user, but not another). Pathogens may include microbes part of an active infection of the user. Pathogens may include microbes that have colonized user and not part of an ongoing infection and are not invading tissue. Pathogens may include opportunistic pathogens, or microbes that may be part of microbiome profile that may cause imminent disease in the user if provided the opportunity.

Continuing in reference to FIG. 1, generating a pathogen index may include training a pathogenicity machine-learning model using a pathogenicity machine-learning process and training data which includes a plurality of data entries of microbiome profile data from subsets of users correlated to indexing values for identifying pathogenic microbes. Pathogenicity machine-learning model 122 may include any machine-learning algorithm, model, and the like, as described in further detail below. Pathogenicity machine-learning process 124 may include any machine-learning process, algorithm, or the like, as performed by a machine-learning module described below. Training data for generating pathogen index 120 may originate from any place as described herein, and may include data relating the severity of symptoms, amount of organism needed to establish infection (IC50, LD50, and the like), relating to a plurality of microorganisms. Such training data may be used to train pathogenicity machine-learning model 122 to derive an index, such as a scoring function, for assigning "pathogenicity" to a plurality of microbes. Such an index may include numerical values, "pathogen"/"non-pathogen" designations, and the like Such a trained machine-learning model may extrapolate a pathogenicity index based on similarity of species, for instance in non-limiting illustrative examples, a user may harbor varying isolates of *Clostridium* spp., where *C. difficile, C. botulinum*, and *C. tetani* may have pathogenicity indexes due to prevalence of disease, vaccination, and study, whereas the pathogenicity index variety of *Clostridium*, or even *Firmicutes*, commensal isolates may be extrapolated, as they relate to pathogens. Pathogen index 120 may be determined from a subset of alike users, where pathogenicity machine-learning model 122 may be trained with training data that includes thousands of user's microbiome organisms as it relates to symptomology, medical history, and the like Such data may be generated by a classifier, where subsets of data are used to train pathogenicity machine-learning model 122 to identify pathogen identities, and assign indexing values as a function of pathogen severity, pathogen incidence, and the like In this way pathogenicity machine-learning model 122 may identify microorganisms that are uniquely pathogenic, according to user; alternatively or additionally, pathogenicity machine-learning model 122 may also identify infection and/or colonization in a user that was not previously identified.

Continuing reference to FIG. 1, computing device 102 may assign the pathogen index 120 to each element in the microbiome profile 106 of the user according to the pathogen index 120 and the pathogenicity machine-learning model 122. If pathogen is identified, it may be labeled for "microbe reduction plan." This may be done using a mathematical operation, such as subtraction. For instance and without limitation, microbes may be assigned a pathogen index numerical value, wherein microorganisms are provided values on a [0, 100] index based on pathogenicity, or propensity to cause infection, likelihood to be found in healthy subsets of users, and the like Microorganisms identified as pathogens may thus retain higher values according to a cutoff threshold, for instance values >60 are considered pathogenic. In such an instance, computing device 102 may subtract each datum in microbiome profile, wherein each datum may be assigned a pathogen index, from a microbiome profile average according to a subset of healthy users. This may result in low scores, or potentially zeros, in places where a beneficial pathogen was matched up to microbiome profile, such as a pathogen-to-pathogen comparison via pairwise alignment, resulting in the positive identification of a pathogen. Similar negative selection process(es) for pathogens may be performed. Such a "subset of healthy users," may include controls for age such as +/−5 years of user current age, fitness level for instance only in users who exercise regularly, body mass index (e.g. only users >10 BMI, and <25 BMI), and the like This may be performed to identify potential sources of bacterial infection more accurately and/or to locate potentially beneficial isolates lacking from user microbiome.

Continuing in reference to FIG. 1, identifying at least a first microbe 118 may include generating a pathogenic microbiome standard, wherein generating the pathogenic microbiome standard may include training a pathogenicity classifier using a pathogenicity classification machine-learning process and training data which includes a plurality of data entries of microbiome profile data from subsets of users correlated to microbe categories based on pathogenicity. A "pathogenic microbe standard," as used in this disclosure, is a microbiome reference that is used to measure microbiome pathogenicity. A pathogenic microbe standard 126 may include a listing of microbiome organisms that may be found in particular subsets of users. A particular "subset of users" for a pathogenic microbe standard 126 may include users that are alike or different from user, categorized based on sex, fitness level, diet, age, medical history, diagnoses, symptoms, among other categorizations based on microbe indicator 104, microbiome profile 106, microbe category 110, among other categorizations. Data relating to microbes present in users may be classified using pathogenicity classifier 128. Pathogenicity classifier 128 may include any classifier as described herein. Pathogenicity classification machine-learning process 130 may include any machine-learning process, algorithm, and the like, as performed by machine-learning module in further detail below.

Continuing in reference to FIG. 1, training data for pathogenicity classifier 128 may include microbiome profile 106 data of a plurality of users correlated to microbe categories based on pathogenicity. Training data may include any data entries, data types, and/or data arrangements as described herein. Training data may originate from any source as described herein. Training data may include a plurality of microbiome profile data from a plurality of users correlated to pathogenic microbes in the plurality of users. In non-limiting illustrative examples, pathogenicity classifier 128 may be trained with a plurality of data entries that correlate microbes, which have been indexed according to pathogenicity using pathogen index 120 among healthy adults, so that outliers may be more easily identified. Outliers may represent novel bacterial isolates, new bacterial strains, rare commensal isolates, public health risks, and the like. Pathogenicity classifier 128 trained in such a manner may identify patterns in the training data the assist in classification of microbes based on propensity to cause infection. This way, computing device 102 may automatically accept a user's microbiome profile 106 as an input and use pathogenicity classier 156 to derive how to identify true pathogens more accurately according to pathogenic microbiome standard 156.

Continuing in reference to FIG. 1, identifying at least a first microbe 118 may include determining a pathogenicity threshold from the pathogenic microbiome standard 126. A "pathogenicity threshold," as used in this disclosure, is a cutoff threshold determined from the pathogen index 120 and the pathogenic microbiome standard 126 for comparing microbiome profile(s) 112 for identifying pathogen microorganisms. For instance and without limitation, pathogenicity threshold may include a numerical value, function of values, mathematical expression, and the like which indicates a value, above which a microorganism may be identified as a pathogenic microbe that represents a first microbe 118 to be eliminated. In non-limiting illustrative examples, pathogenicity threshold may include a tiered numerical value system, wherein pathogenicity threshold dictates that microbes with pathogenicity index <20 are non-pathogenic and >75 should be eliminated. Pathogenicity threshold may be determined from pathogenicity classifier 128 according to observations about the incidence rate of microbes in health cohorts.

Continuing in reference to FIG. 1, identifying the at least a first microbe 118 may include comparing the microbiome profile 106 of the user to the pathogenicity threshold. Pathogenicity threshold may be generated as a function of the pathogenic microbiome standard 156 and the pathogenicity classifier 128. Computing device 102 may compare microbiome profile 106 and pathogenicity threshold identify microorganisms that correlate to infection and/or represent pathogenic organisms. Computing device 102 may compare microbiome profile 106 and pathogenic microbiome standard 156 by comparing the strings representing organism identities between lists to identify microbes that match, wherein organisms that match will be added to microbiome reduction strategy 132. Computing device 102 may compare a pathogen-indexed microbiome profile 106 to pathogenicity threshold, pathogen index 120, or pathogenic microbiome standard 156, to identify pathogens. A "pathogen indexed microbiome profile," as used in this disclosure, is a microbiome profile 106 of a user that has been indexed according to pathogen index 120 for comparing to pathogenicity threshold. For instance, if an organism exists in microbiome profile 106 that does not match pathogenic microbiome standard 156 computing device may derive a pathogenicity solution according to scoring criteria derived from the pathogen index 120 and the pathogenicity threshold.

Continuing in reference to FIG. 1, identifying the at least a first microbe 118 may include identifying the at least a first microbe 118 as a function of the comparison. Computing device 102 may compare microbiome profile 106 and pathogenic microbiome standard by determining a pathogenic threshold value. For instance and without limitation the comparison may include a threshold numerical value, above which a microorganism is identified as a pathogen. In such an instance, a threshold value may be derived from the pathogenicity classifier 128, wherein a minimal pathogen index 120 value is identified, as microbiomes are classified according to prevalence among a cohort of users (e.g. among healthy adults, and the like).

Continuing in reference to FIG. 1, determining a microbe reduction strategy 116 includes determining at least a first nutrient amount that aids in reduction of the at least a first microbe 118. First microbe 118 may include a microbe identified as a function of locating opportunistic pathogenicity potential, digestive issues, for instance using microbiome indicator(s) 108. A "first nutrient amount," as used in this disclosure, is a quantity of a nutrient amount intended to reduce the population of a first microbe 118. A first nutrient amount 132 may include a mass amounts of a vitamin, mineral, macronutrient (carbohydrate, protein, fat), a numerical value of calories, mass amounts of phytonutrients, antioxidants, bioactive ingredients, probiotics, active cultures, nutraceuticals, and the like.

Continuing in reference to FIG. 1, determining at least a first nutrient amount that aids in reduction of the at least a first microbe 118 may include training a reduction model using a reduction machine-learning process and training data, wherein training data includes a plurality of data entries of nutrition amounts correlated to reducing microbial populations. A "reduction model," as used in this disclosure, is a machine-learning model that may be trained to determine nutrient amounts that may reduce populations of a pathogenic microorganism. Reduction machine-learning process 136 may include any machine-learning process, algorithm, and/or model as performed by a machine-learning model described in further detail below. Reduction machine-learning process 136 may include, for instance using a machine-learning process and/or method (e.g. supervised learning) to train a machine-learning model (e.g. neural net, naïve Bayes algorithm, and the like) with training data that includes a plurality of data entries that correlate nutrients amounts to pathogen colonization. Training data for reduction model 134 may include a plurality of data that includes food items, supplements, probiotics, and the like as they may relate to growth rates, CFU/mL, selectively pressure, and the like, for microorganisms. Such training data may originate from any source described herein; for instance peer-reviewed research may include data that describes effects on microbiome health from consuming a variety of products such as animal products, organic vs non-organic fruits, vegetables, grains, use of GMOs vs non-GMO products, and the like Continuing in reference to FIG. 1, reduction model 134 training data may include a plurality of data entries including nutrient identities (e.g. nutrition elements), nutrient amounts (e.g. nutrition facts from food, mg/kg nutraceuticals, phytonutrients, bioactive ingredients, microbial populations, and the like), wherein the data entries are associated with effects on colonization of pathogens. Such training data may include nutrient amounts that prevent attachment and colonization of the gut epithelial by pathogens, foods that improve mucous and glycan production by epithelial cells, nutrients that support IgA and IgG recruitment, for instance form Peyer's Patches, lymph, and the like Such training data may include nutrient amounts of a plurality of nutrients with proposed roles in infection such as zinc, calcium, and other minerals, water-soluble and fat-soluble vitamins, particular carbohydrates, and the like, wherein training data may relate nutrient amounts from in vivo and in vitro studies to effects on bacterial cell death, CFU/mL, or any effect on a pathogen.

Continuing in reference to FIG. 1, determining the at least a first nutrient amount 132 that aids in reduction of the at least a first microbe 118 may include determining the at least a first nutrient amount 132 as a function of the at least a first microbe 118 and the reduction model 134. Computing device 102 may accept an input of at least a first microbe 118 and output at least a first nutrient amount 132 intended to reduce the population and/or eventually eliminate the pathogen from the user's current microbial colonization state. Such an output of at least a first nutrient amount 132 may include a frequency and magnitude organized into a schedule for reducing the population and/or eliminating the pathogen from the microbiome profile 106. A "frequency," as used in this disclosure, is a number of consumption occurrences associated with a time course, such as daily, weekly, monthly, and the like, of which a nutrition element is intended to be consumed. Frequency may be determined as a function of the identified effect in microbe reduction strategy 116, wherein the frequency of consumption is tailored to provide a sufficient minimal nutrient level over a time A "magnitude," as used in this disclosure, is a serving size of at least a nutrition element as a function of the identified effect. Identifying the magnitude associated with the at least a nutrition element may include calculating a serving size of the at least a nutrition element as a function of the identified effect in the microbe reduction strategy 116. A nutrition element magnitude may include a calculated nutrient amount. Nutrient amounts may include dosages, for instance and without limitation, a particular dosage of NSAIDs (mg/kg), gluten (g/day), and the like Determining the at least a first nutrient amount 132 may include retrieving a nutrient amount from a database, such as a microbiome database described in further detail below. For instance, a plurality of nutrient amounts may be stored in a database wherein computing device 104 may look-up nutrient amounts as necessary.

Continuing in reference to FIG. 1, computing device 102 is configured to determine at least a first nutrition element 138, wherein the at least a first nutrition element 138 includes the at least a first nutrient amount 132. A "nutrition element," is an item that includes a nutrient intended to be used and/or consumed by user. A first nutrition element 138 may include consumed foods, medications, stimulants, supplements, probiotics, and the like that may contribute to eliminating a first microbe 118 and/or addressing a microbe indicator 104 from microbiome profile 106 (e.g. symptom).

Continuing in reference to FIG. 1, identifying a first nutrition element 138 may include training a machine-learning process with training data, wherein training data includes a plurality of data entries that correlates a plurality of nutrient amounts to a plurality of nutrition elements. Machine-learning process may include any machine-learning process, algorithm, and/or model described herein, as performed by a machine-learning module described in further detail below. Machine-learning process may derive relationships in nutrient amounts that relate to particular nutrition elements, provided that nutrition elements may contain nutrients that aid promoting the pathogen's colonization of the user. For instance and without limitation, nutrients amounts may include nutrients to promote growth of competing organisms, reduce the pathogen population; however, foods with a first nutrient amount 132 may contain nutrients that work antagonistically. Training a machine-learning process may generate a function (or series of functions) which "learn" which nutrition elements work toward eliminating a first microbe 118. Such training data may include nutrition facts of nutrition elements as it relates to promoting or suppressing growth of a variety of microorganisms. Training data may include a plurality of data entries that correlates nutrient amounts and their associated effects to microbe category 110. Such training data may include vitamin and mineral amounts to address particular bacterial infections. A machine-learning model trained with such data may "learn" to output a first nutrition element 138 as a function of input (first nutrient amount 132). Such training data may originate from any source as described herein, such as from a database, web browser and the Internet, the user, wearable device, a physician, medical history, biological extraction test result, and the like Continuing in reference to FIG. 1, identifying a first nutrition element 138 may include calculating the at least a nutrient amount as a function of the microbe category 110 of the user. Calculating a nutrient amount may include using a trained machine-learning process to automatically calculate nutrient amounts (e.g. mg/kg, mg/cal, mg/g macromolecule, and the like) as a function of the pathogen to be eliminated (input). Calculating nutrient amounts in this manner may include deriving functions, equations, and the like, from relationships observed in the training data between pathogen survivability and nutrients.

Continuing in reference to FIG. 1, computing device 102 may calculate a nutrient amount, for instance, by using a default amount, such as from a standard 2,000 calorie diet, and increasing and/or decreasing the amount according to a numerical scale as it relates to a pathogen (or beneficial microorganism). Such a calculation may include a mathematical operation such as subtraction, addition, multiplication, and the like; alternatively or additionally, such a calculation may involve deriving a loss function, vector analysis, linear algebra, system of questions, and the like, depending on the granularity of the process. Nutrient amounts may include threshold values, or ranges or values, for instance and without limitation, derived from classified of subsets of users, as described above. Nutrient amounts may be calculated as heat maps (or similar mathematical arrangements), for instance using banding, where each datum of microbiome profile 106 (e.g. pathogen to be eliminated) elicits a particular range of a particular nutrient amount or set of amounts. In non-limiting illustrative examples, such a calculation may include querying for and retrieving a standard amount of water soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 102 may store and/or retrieve the above standard nutrient amounts, for instance in a database. The amounts may be re-calculated and converted according to a user's microbiome profile 106. For instance, these amounts may relate to an average BMI, older male, classified to microbe category 110 indicating a particular pathogen to be eliminated, but may be adjusted according to unique user-specific microbe indicators 104. For example, an obese woman who has been placed on a strict 1,600 Calorie/day diet, curated according to identified risk factors (microbe indicators 104) may need the above amounts recalculated according to the calorie constraint (threshold), where some vitamin amounts may increase, some may decrease, and some may remain constant according to the pathogen to be eliminated.

Continuing in reference to FIG. 1, computing device 102 may identify the first nutrition element 138 by using a first nutrient amount 174 as an input and generating combinations, lists, or other aggregates of nutrition elements necessary to achieve nutrient amount. For instance, computing device 102 may use a template nutrient amount of '200 mg vitamin C' and build a catalogue of nutrition elements until the 200 mg vitamin C value is obtained. Computing device 102 may perform this task by querying for food items, for instance from a menu, grocery list, or the like, retrieving the vitamin C content, and subtracting the value from the nutrient amount. In non-limiting illustrative examples, computing device 102 may identify orange juice (90 mg vitamin C/serving; 200 mg−90 mg=110 mg) for breakfast, Brussel sprouts (50 mg vitamin C/serving; 110 mg−50 mg=60 mg) for lunch, and baked potato (20 mg vitamin C/serving) and spicy lentil curry (40 mg vitamin C/serving; 60 mg−(20 mg+40 mg)=0 mg) for dinner. In such an example, computing device 102 may search according to a set of instructions including for instance and without imitation food preferences, allergies, restrictions, pathogen reduction, and the like, present in a microbiome profile 106, provided by a physician, user, or the like, and subtract each identified nutrition element from nutrient amount until a combination of nutrition elements that represents a solution is found. Once a solution is found, computing device 102 may generate a file of nutrition elements and store in a database, as described in further detail below.

Continuing in reference to FIG. 1, computing device 102 is configured to determine, using the microbe category 110 and the microbiome profile 106, a microbiome supplementation program. A "microbiome supplementation program," as used in this disclosure, is a strategy including at least a nutrient amount intended to be taken by the user to support the population of a microorganism. Supporting a population of a microorganism may include increasing the population of a microorganism until colonization is able to be established in user. Supporting a population of a microorganism may include introducing an exogenous microbial species to a user's microbiome. Supporting a population of a microorganism may include bolstering a population of a microorganism already found in and/or on a user. A microbiome supplementation program 140 may include a microorganism identifier such as the genus, species, and the like, a status including current level of microbe, the presence of microbe, incidence in user population, and the like, nutrient amounts and/or nutrition elements associated with supporting microbial populations.

Continuing in reference to FIG. 1, determining the microbiome supplementation program 140 includes identifying at least a second microbe to be included to the microbiome profile according to the classification. A "second microbe," as used in this disclosure, is at least one microorganism, microorganism type, and the like, that has been identified to be supplemented to microbiome profile 106 of a user. It is important to note that one may want to reduce the population and/or colonization of some microbes and increase others. For instance, *Clostridium* species, as a predominant cluster of commensal bacteria in the human gut, exert a wealth of salutary effects on intestinal homeostasis. *Clostridium* spp. have been long reported to attenuate inflammation and allergic diseases effectively owing to their distinctive biological activities. Their cellular components and metabolites, such as butyrate, secondary bile acids, and indole propionic acid, play a probiotic role primarily through energizing intestinal epithelial cells, strengthening intestinal barrier and interacting with immune system. In turn, dietary habits and physical state may shape unique patterns of *Clostridium* spp. in gut. In such an example, there may exist several *Clostridium* spp. that a user may wish to increase and/or supplement to their microbiome; however, some *Clostridium* spp. such as *C. difficile*, represent severe pathogens. The benefit *Clostridium* spp. pose to human gut flora may be achieved by supplementing certain microbial species, while reducing others, even within the same genus.

Continuing in reference to FIG. 1, identifying at least a second microbe 142 may include generating a balancing index, wherein generating the balancing index includes training a microbe balancing machine-learning model using a microbe balancing machine-learning process and training data which includes a plurality of data entries of microbiome profile data from subsets of users correlated to indexing values for identifying beneficial microbes. A "balancing index," as used in this disclosure, is a systematic index used to classify a microorganism as beneficial to a user's microbiome. Balancing index 144 may include a scoring index, repository, listing, and the like, of microbes (bacteria, protists, yeasts, and the like) that represent beneficial microorganisms for user. Beneficial microorganisms may be user-specific (one bacterial isolate may represent a benefit for a particular user, but a pathogen for another). Beneficial microorganisms may include probiotics part of a healthy user's microbiome (e.g. as indicated by microbe indicator 104 from a classification among a cohort of users). A microbe balancing machine-learning model 146 may include any machine-learning algorithm, model, or the like, as described herein. Microbe balancing machine-learning process 148 may include any machine-learning process, algorithm, and/or model, and the like, as performed by a machine-learning module as described in further detail below. Training data for training microbe balancing machine-learning model 146 may include training data as described above for pathogenicity machine-learning model 122. Training data may include, for instance and without limitation, microorganisms correlated to varying degrees of beneficial symbiotic relationships with users. Such relationships may include digestion, competition with opportunistic pathogens, among many others. Training data may include classified microbiome profiles 106, wherein microorganism identities are classified as a function of 1) microorganisms identified among healthy adults, and 2) microorganisms that have low pathogen index 120 scores. Training data may include microorganisms correlated to digestive ability for instance homo- and heterofermentative bacteria, xylose digestion, and the like. Training data may originate from any source descried herein such as a database, web browser and the Internet, peer-reviewed research database, physician, user input, and the like Such training data may be used to train microbe balancing machine-learning model 146 to derive a function, equation, or the like, from relationships observed in the training data, for instance and without limitation, that result in patterns of identification of novel beneficial microbial species as a function of their presence in cohorts of healthy adults.

Continuing in reference to FIG. 1, identifying at least a second microbe 142 may include generating a balancing standard, wherein generating the balancing standard may include training a microbe balancing classifier using a balancing classification machine-learning process and training data which includes a plurality of data entries of microbiome profile data from subsets of users correlated to microbe categories based on incidence of microbes. A "balancing standard," as used in this disclosure, is a microbiome reference that is used to measure microorganism benefit to user according to presence in microbiome. A balancing standard 150 may include a listing of microbiome organisms that may be found in a particular subset of users. A "particular subset of users" for a balancing standard 150 may include users that are alike or different from user, categorized based on sex, fitness level, diet, age, medical history, diagnoses, symptoms, among other categorizations based on microbe indicator 104, microbiome profile 106, microbe category 110, and the like. For instance, if user were diagnosed with a bacterial infection, overweight, diabetic, and the like, a subset of healthy users lacking bacterial infection, at healthy BMI, non-diabetic, and the like, may be used to generate a balancing standard 150 to compare against. In non-limiting illustrative examples, a subset of users to derive a balancing standard 150 for a microbiome profile indicating a user is diabetic may include classification among a cohort of users that have adjusted to diabetes but are otherwise healthy. This way, identification of isolates that may assist in disease management may be identified. Data relating to microbes present in users may be classified using balancing classifier 152. Balancing classifier 152 may include any machine-learning classifier, as described herein. Balancing classification machine-learning process 154 may include any machine-learning process, algorithm, and the like, as performed by machine-learning module described in further detail below. Training data for generating balancing classifier 152, for instance and without limitation, may include data that correlates symbiotic abilities of microorganisms with their colonization of the human gut; in this way, bacterial isolates may be classified according to digestive capabilities, protection against pathogens, association with disease states, and the like Continuing in reference to FIG. 1, identifying at least a second microbe 142 may include determining a balancing threshold from the balancing standard 150. A "balancing threshold," as used in this disclosure, is a cutoff threshold determined from the balancing index 144 and the balancing standard 150 for identifying beneficial microorganisms. For instance and without limitation, balancing threshold may include a numerical value, function of values, mathematical expression, and the like which indicates a value, above which a microorganism may be identified as a beneficial microbe that represents a second microbe 142 to be supplemented to user's microbiome profile 106. In non-limiting illustrative examples, balancing threshold may include a tiered numerical value system, wherein balancing threshold dictates that microbes with balancing index <20 are not very beneficial and >75 should be part of a user's microbiome. Balancing threshold may be determined from balancing classifier 152 according to observations about the incidence rate of microbes in health cohorts.

Continuing in reference to FIG. 1, generating the balancing index 144 may include assigning the balancing index 144 to each element in the microbiome profile 112 of the user. Microbiome profile 112 may have associated with each datum (e.g. microorganism species) a pathogen index 120 and/or balancing index 144. For instance, a high balancing index score may indicate a highly beneficial microorganism that may be missing from user microbiome, or a microorganism found in user microbiome that is highly correlated among healthy adults. Assigning balancing index 144 may be performed as described above for pathogen index 120.

Continuing in reference to FIG. 1, identifying at least a second microbe 142 may include comparing the microbiome profile 106 of the user to the balancing standard generated by the microbe balancing classifier 152. Balancing threshold may be generated as a function of the balancing standard 150 and the balancing classifier 152. Computing device 102 may compare microbiome profile 106 and balancing threshold to identify microorganisms that correlate to ameliorating a current symptom in the user (e.g. lactose intolerance, dry skin, and the like) and/or represent organisms highly correlated among target cohorts. Target cohorts may be healthy adults, adults with a target BMI value, a target visceral fat content, daily caloric intake targets, and the like that is a user is targeting to improve health state. Computing device 102 may compare microbiome profile 106 (balancing indexed) and balancing threshold by comparing the strings (e.g. organism names) between lists to identify microbes that are above a threshold value but are currently absent from user, wherein organisms will be added to microbiome supplementation program 140. Computing device 102 may compare a balancing-indexed microbiome profile 106 to balancing threshold, to identify potentially beneficial microorganisms that are currently present. A "balancing indexed microbiome profile," as used in this disclosure, is a microbiome profile 106 of a user that has been indexed according to balancing index 144 for comparing to balancing threshold. For instance, if an organism exists in microbiome profile 106 that does not match balancing standard 156, then computing device may derive a solution according to scoring criteria derived from the balancing index 144 and the balancing threshold.

Continuing in reference to FIG. 1, identifying the at least a second microbe 142 may include identifying the at least a second microbe 142 as a function of the comparison. Computing device 102 may compare microbiome profile 106 and balancing standard by determining a balancing threshold value. For instance and without limitation the comparison may include a threshold numerical value, above which a microorganism is identified as beneficial. In such an instance, a threshold value may be derived from the balancing classifier 152, wherein the index values are derived, and microbiomes are classified according to prevalence among a cohort of users (e.g. among healthy adults, and the like).

Continuing in reference to FIG. 1, determining a microbiome supplementation program 140 includes determining at least a second nutrient amount that aids in supplementation to microbiome profile of the at least a second microbe 142. A "second nutrient amount," as used in this disclosure, is a quantity of a nutrient amount intended to increase, support, and/or introduce the population of a second microbe 142. A second nutrient amount 156 may include a mass amounts of a vitamin, mineral, macronutrient (carbohydrate, protein, fat), a numerical value of calories, mass amounts of phytonutrients, antioxidants, bioactive ingredients, nutraceuticals, and the like. A second nutrient amount 156 may include a food item, beverage, and/or supplement (e.g. probiotic) intended to introduce a new microorganism into the microbiome of user. Determining at least a second nutrient amount 156 may include retrieving a nutrient amount from a database, such as a microbiome database described in further detail below. For instance, a plurality of nutrient amounts may be stored in a database wherein computing device 104 may look-up nutrient amounts as necessary.

Continuing in reference to FIG. 1, determining the at least a second nutrient amount 156 that aids in supplementation of the at least a second microbe 142 may include training a supplementation model using a supplementation machine-learning process and training data, wherein training data includes a plurality of data entries of nutrition amounts correlated to effects on increasing microbial populations. Supplementation model 158 may include any machine-learning algorithm, model, and the like, as described herein. Supplementation machine-learning process 160 may include any machine-learning process, algorithm, or the like, as described herein and/or performed by a machine-learning module as described in further detail below. Supplementation model 158 training data may include any trading data described herein for machine-learning process, algorithms, and/or models. Training data may originate from any source described herein. In non-limiting illustrative examples, supplementation model 158 training data may include nutrient amounts, nutrition elements, beverages, probiotics, supplements, and the like, correlated with supporting introduction, growth, and/or colonization of a plurality of beneficial microorganisms.

Continuing in reference to FIG. 1, computing device 104 may determine the at least a second nutrient amount 156 as a function of the at least a second microbe 142 and the supplementation model 158. Training data may be used to generate supplementation model 158, which may be trained to derive an equation, function, and the like, that describes relationships observed in the training data for nutrient amounts as it relates to supporting beneficial bacterial species, fungi, protists, amoeba, and the like. Computing device may accept an input of a second microbe 142 and, as a function of the supplementation model 158, output the at least a second nutrient amount 156 that may promote the introduction, growth, and/or colonization of the second microbe 142. Supplementation model 158 may be used to determine a nutrient amount that works synergistically to bolster beneficial species and aid in reduction of pathogenic species, as described above.

Continuing in reference to FIG. 1, determining microbiome supplementation program 140 includes identifying at least a second nutrition element, wherein of the at least a second nutrition element includes the at least a second nutrient amount. A second nutrition element 162 may include consumed foods, medications, stimulants, supplements, probiotics, and the like that may contribute to supporting supplementation of a second microbe 142 to microbiome profile 106. A second nutrition element 162 may be determined in any manner as described herein for first nutrition element 138.

Continuing in reference to FIG. 1, computing device 104 is configured to generate a microbiome balance plan, using the microbe reduction strategy 116 and the microbiome supplementation program 140, wherein the microbiome balance plan includes a frequency and a magnitude for establishing balanced colonization in the user. A "microbiome balance plan," as used in this disclosure, includes dietary recommendations (nutrient amounts, nutrition elements, and the like) intended to balance microbiome profile 106. "Balancing" microbiome profile 106 may include eliminating pathogens, supplementing beneficial microorganisms, and/or combinations thereof. Microbiome balance plan 164 may include a frequency (timing of meals, supplements, and the like) and a magnitude (serving size, nutrient amount, and the like) for establishing balanced colonization in the user. This may include a variety of scheduling paradigms according to how many live organisms, spores, eggs, and the like, of an organism must be introduced to sustain colonization. For instance, introduction may need to be tiered with smaller amounts first being introduced, and gradually increased daily. Once colonization is established with beneficial microorganisms and pathogens have been eliminated, continued exposure of the microorganism may not be necessary. In such a case, relationships observed between nutrient amounts, nutrition elements, and pathogens and/or beneficial isolates, as determined by machine-learning models described herein, may be utilized to accurately define microbiome balance plan 164 terms and conditions.

Continuing in reference to FIG. 1, generating the microbiome balance plan 164 may include generating an objective function with the at least a first nutrition element 138 and the at least a second nutrition element 162 wherein the objection function outputs at least an ordering of a plurality of nutrition elements according to constraints from the microbe reduction strategy 116 and the microbiome supplementation program 140. An "objective function," as used in this disclosure, is a mathematical function that may be used by computing device 102 to score each possible combination of nutrition elements, wherein the objective function may refer to any mathematical optimization (mathematical programming) to select the 'best' element from a set of available alternatives. Selecting the 'best' element from a set of available alternatives may include a combination of nutrition elements which achieves the nutrient amounts in addressing microbe reduction strategy 116, microbiome supplementation program 140, microbiome profile 106 in a user.

Continuing in reference to FIG. 1, in non-limiting illustrative examples, an objective function may include performing a greedy algorithm process. A "greedy algorithm" is defined as an algorithm that selects locally optimal choices, which may or may not generate a globally optimal solution. For instance, computing device 104 may select combinations of nutrition elements so that values associated therewith are the best value for each category. For instance, in non-limiting illustrative example, optimization may determine the combination of the most efficacious 'serving size', 'timing of consumption', 'probiotic product', 'phytonutrient', and the like, categories to provide a combination that may include several locally optimal solutions but, together, may or may not be globally optimal in combination.

Still referring to FIG. 1, in further non-limiting illustrative examples, objective function may be formulated as a linear objective function, which computing device 102 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user (e.g. lactose intolerance, poor absorption, food allergy, and the like), and a linear program may use a linear objective function to calculate ingredient combinations, considering how these limitations effect combinations. In various embodiments, system 100 may determine a set of instructions towards building microbiome balance plan 164 that maximizes a total bacterial infection prevention score subject to a constraint that there are other competing objectives. Such a score may include a summation of pathogen index 120 and balance index 144 for each element in microbiome profile 106, wherein "maximizing" the score may be performed according to the numerical scale, and what criteria is used for "high" and "low" scores. For instance, if achieving one nutrient amount and a second nutrient amount may result in needing to select a first nutrition element and a second nutrition element, wherein each may compete in balancing microbiome (e.g. adopting two or more diet types simultaneously may not be feasible, boosting beneficial microbe that boosts pathogen may not be feasible, and the like). A mathematical solver may be implemented to solve for the set of instructions that maximizes scores; mathematical solver may be implemented on computing device 102 and/or another device in system 100, and/or may be implemented on third-party solver.

With continued reference to FIG. 1, in further non-limiting illustrative examples, objective function may include minimizing a loss function, where a "loss function" is an expression of an output which a process minimizes to generate an optimal result. For instance, achieving a first nutrient amount 138 and a second nutrient amount 156 may be set to a nominal value, such as '100', wherein the objective function selects elements in combination that reduce the value to '0', wherein the nutrient amounts are '100% achieved'. In such an example, 'maximizing' would be selecting the combination of nutrition elements that results in achieving nutrient amounts by minimizing the difference, where suboptimal pairing results in score increases. As a non-limiting example, computing device 102 may assign variables relating to a set of parameters, which may correspond to microbiome balance plan 164 components, calculate an output from a mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Figure 2:
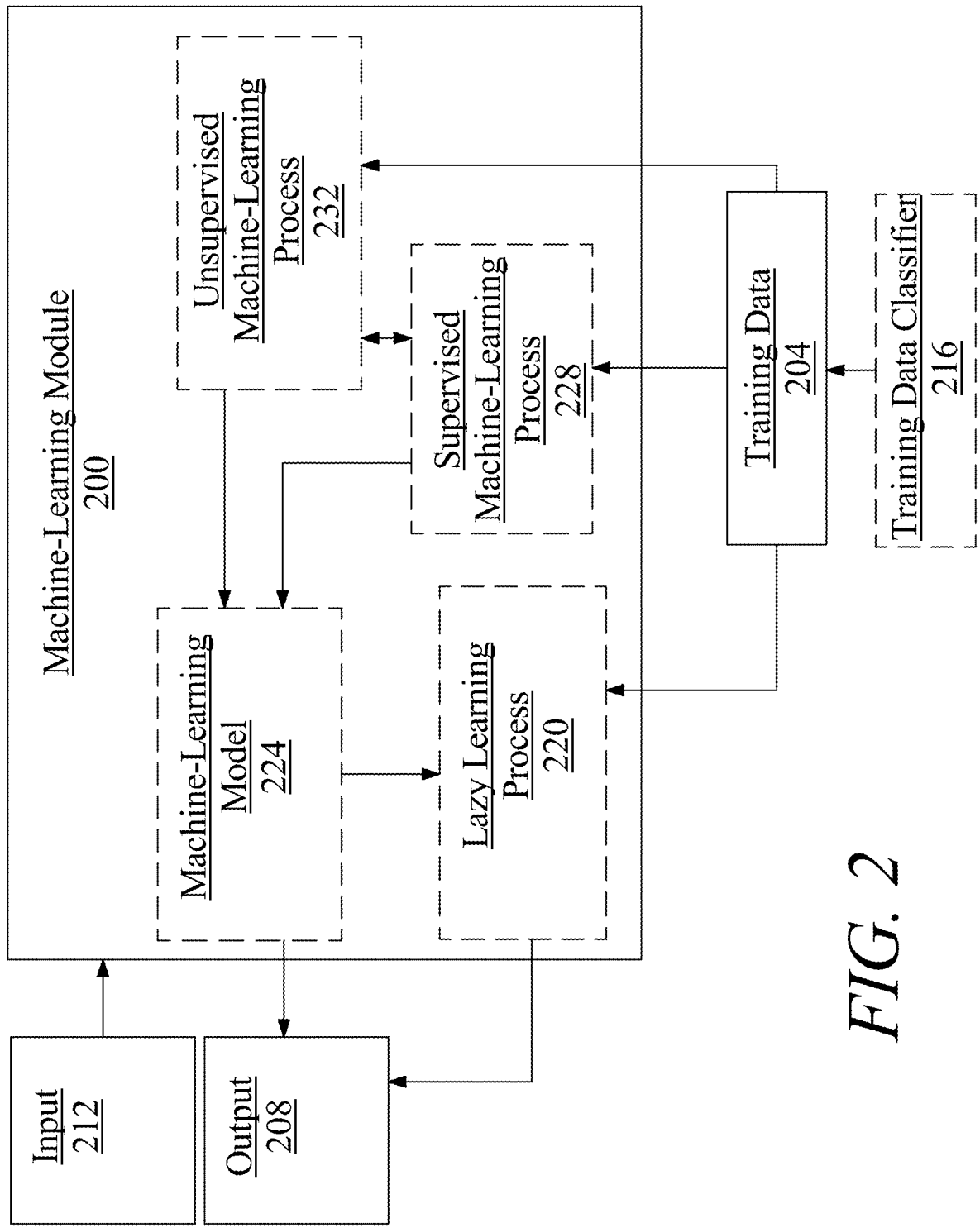
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of microbe indicators 104 (such as patterns in cytokine levels, bacterial isolates, gene expression, and the like, as it relates to microbiome profile 106) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying microbe indicator 104 elements to microbiome profile 106 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network including an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to microbiome profile 106, pathogen index 120, balancing index 144, and the like, as described herein, to "learn" the upper and lower limits to the numerical scale, the increments to providing scoring, and the criteria for increasing and decreasing elements encompassed in the microbiome profile 106, pathogen microbe standard 126, balancing standard 150, and the like A machine-learning model may be used to "learn" which elements of microbe indicators 104 have what effect on microbiome profile 106, and which elements of microbiome profile 106 are affected by particular nutrition elements and the magnitude of effect, and the like The magnitude of effect may be enumerated and provided as part of system 100, where nutrition elements are communicated to user for their microbiome properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a microbiome profile 106 (potentially classified into microbe categories 110), as described above as inputs, nutrient amount outputs, and a ranking function representing a desired form of relationship to be detected between inputs and outputs; ranking function may, for instance, seek to maximize the probability that a given input (such as nutrient amounts) and/or combination of inputs is associated with a given output (reducing pathogen, increasing beneficial microbe, and the like, that are 'best' for microbe category 110) to minimize the probability that a given input is not associated with a given output, for instance finding the most suitable times to consume meals, and what the meals should be, and the like Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network including an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
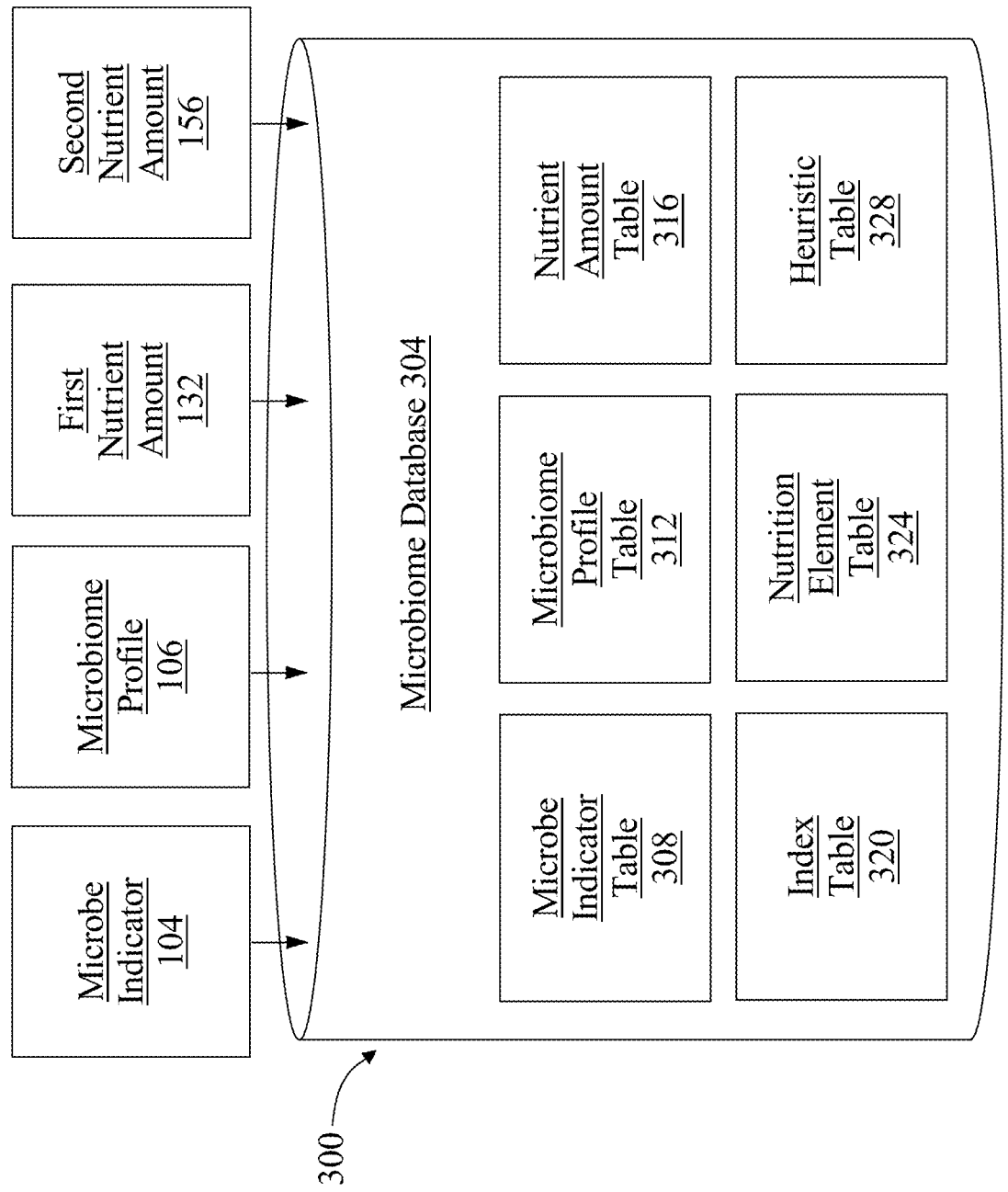
FIG. 3 is a block diagram of a microbiome database.

Referring now to FIG. 3, a non-limiting exemplary embodiment 300 of a microbiome database 304 is illustrated. Microbe indicator 104 for a plurality of subjects, for instance for generating a training data classifier 216, may be stored and/or retrieved in microbiome database 304. Microbe indicator 104 data from a plurality of subjects for generating training data 204 may also be stored and/or retrieved from microbiome database 304. Computing device 102 may receive, store, and/or retrieve training data 204, wearable device data, physiological sensor data, biological extraction data, and the like, from microbiome database 304. Computing device 102 may store and/or retrieve machine-learning models, classifiers, among other determinations, I/O data, heuristics, algorithms, and the like, from microbiome database 304.

Continuing in reference to FIG. 3, microbiome database 304 may be implemented, without limitation, as a relational database, a key-value retrieval database such as a NOSQL database, or any other format or structure for use as a database that a person skilled in the art would recognize as suitable upon review of the entirety of this disclosure. Microbiome database 304 may alternatively or additionally be implemented using a distributed data storage protocol and/or data structure, such as a distributed hash table and the like. Microbiome database 304 may include a plurality of data entries and/or records, as described above. Data entries in microbiome database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, microbiome database 304 may include, without limitation, microbe indicator table 308, microbiome profile table 312, nutrient amount table 316, index table 320, nutrition element table 324, and/or heuristic table 328. Determinations by a machine-learning process, machine-learning model, ranking function, and/or classifier, may also be stored and/or retrieved from the microbiome database 304. As a non-limiting example, microbiome database 304 may organize data according to one or more instruction tables. One or more microbiome database 304 tables may be linked to one another by, for instance in a non-limiting example, common column values. For instance, a common column between two tables of microbiome database 304 may include an identifier of a submission, such as a form entry, textual submission, accessory device tokens, local access addresses, metrics, and the like, for instance as defined herein; as a result, a search by a computing device 102 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of microbiome database 304 may include, as a non-limiting example, microbe indicator table 308, which may include categorized identifying data, as described above, including genetic data, epigenetic data, microbiome data, physiological data, biological extraction data, and the like. Microbe indicator table 308 may include microbe indicator 104 categories according to gene expression patterns, SNPs, mutations, cytokine concentration, allergen data, data concerning metabolism of nutrition elements 144, pharmacokinetics, nutrient absorption, and the like, categories, and may include linked tables to mathematical expressions that describe the impact of each microbe indicator 104 datum on microbiome profile 106, for instance threshold values for gene expression, and the like, as it relates to immunological function, microbe category 110, and the like Microbe indicator table 308 may include genus, species, serotype, and the like, listing of bacterial isolates, fungi, viruses, parasites, amoeba, among other microorganisms. One or more tables may include microbiome profile table 312, which may include data regarding microbe indicator 104, thresholds, scores, metrics, values, categorizations, and the like, that system 100 may use to calculate, derive, filter, retrieve and/or store microbe categories 110, pathogens, beneficial microorganisms, identifiers related with cohorts, and the like. One or more tables may include nutrient amount table 316, which may include data on nutrient amounts for instance classified to microbe category 110, classified to data from alike users with similar microbe indicator(s) 104 and/or microbiome profile 106, and the like, that system 100 may use to calculate, derive, filter, retrieve and/or store nutrient amounts. Nutrient amounts may include nutrients related to eliminating pathogens, supporting beneficial microorganisms, introducing new microorganisms to microbiome, and the like One or more tables may include index table 320, which may include functions, model, equations, algorithms, thresholds, and the like, used to calculate or derive pathogen index 120, pathogen microbe standard 126, balancing index 144, balancing standard 150, among other indices, standards, and the like One of more tables may include nutrition element table 324, which may include nutrition element identifiers, microbe reduction and/or microbiome supplementation program strategy, associated nutrient amounts and/or nutrition elements for reducing microorganism populations, frequency and magnitudes associated with nutrition elements, regarding times to eat, identifiers of meals, recipes, ingredients, diet types, and the like. One or more tables may include, without limitation, a heuristic table 328, which may organize rankings, scores, models, outcomes, functions, numerical values, scales, arrays, matrices, and the like, that represent determinations, probabilities, metrics, parameters, values, standards, indexes, and the like, include one or more inputs describing potential mathematical relationships, as described herein.

Referring now to FIGS. 4A and 4B, a non-limiting exemplary embodiment 400 of a microbiome profile 106 is illustrated. Microbiome profile 106 may include a variety of microbe indicator 104 categories, for instance 22 distinct categories, as shown in FIGS. 4A and 4B. each microbe indicator 104 may be assigned a parameter and/or value, such as an arbitrary value, where some microbe indicators 104, such as those shaded in light grey, may relate to absolute scales from [0, x], where x is a maximal value and the range of values for the microbe indicator 104 cannot be below a 'zero amount'. Some microbe indicators 104, such as those shaded in dark grey, may relate to gene expression levels, wherein, the microbe indicator 104 is enumerated as a 'box plot' that illustrates the range of expression in a population of users organized according to, for instance tissue type. In such an example, the dashed line may relate to a 'normal threshold' above which is elevated gene expression of the user, below which is decreased expression level. Each microbe indicator 104 may have associated with it a numerical score, or some other identifying mathematical value that computing device 102 may assign. Persons skilled in the art, upon benefit of this disclosure in full, may appreciate that for each user, any number of microbe indicators 104 may be enumerated and assigned a value according to microbiome profile machine-learning model 108. Microbiome profile 106 may be graphed, or otherwise displayed, according to the enumeration by microbiome profile machine-learning model 108. For instance, each bar of the bar graph, or combinations of bar graph categories, may instruct a classification of a user's microbiome profile 106 to microbe category 110.

Still referring now to FIGS. 4A and 4B, in non-limiting exemplary illustrations microbiome profile 106 may be classified to microbe category 110. Some and/or all of the microbe indicators 104 summarized in microbiome profile 106 may be used to classify an individual to a particular microbe category 110. For instance, as shown in FIG. 4B, ten of the 22 microbe indicator 104 categories may be used to classify microbiome profile 106 to one or more subsets of bacterial isolates, for instance, categorization based on cyanobacteria, chlamydia (obligate intracellular), acidobacteria, among others, based on pathogenicity categorizations, and the like Alternatively or additionally, microbiome profile machine-learning model 108 may be trained to assign microbe indicator 104 to microbe category 110, wherein computing device 102 may know the identity of microbe category 110 according to which microbe category 110 has the most identifying data points.

Figure 5:
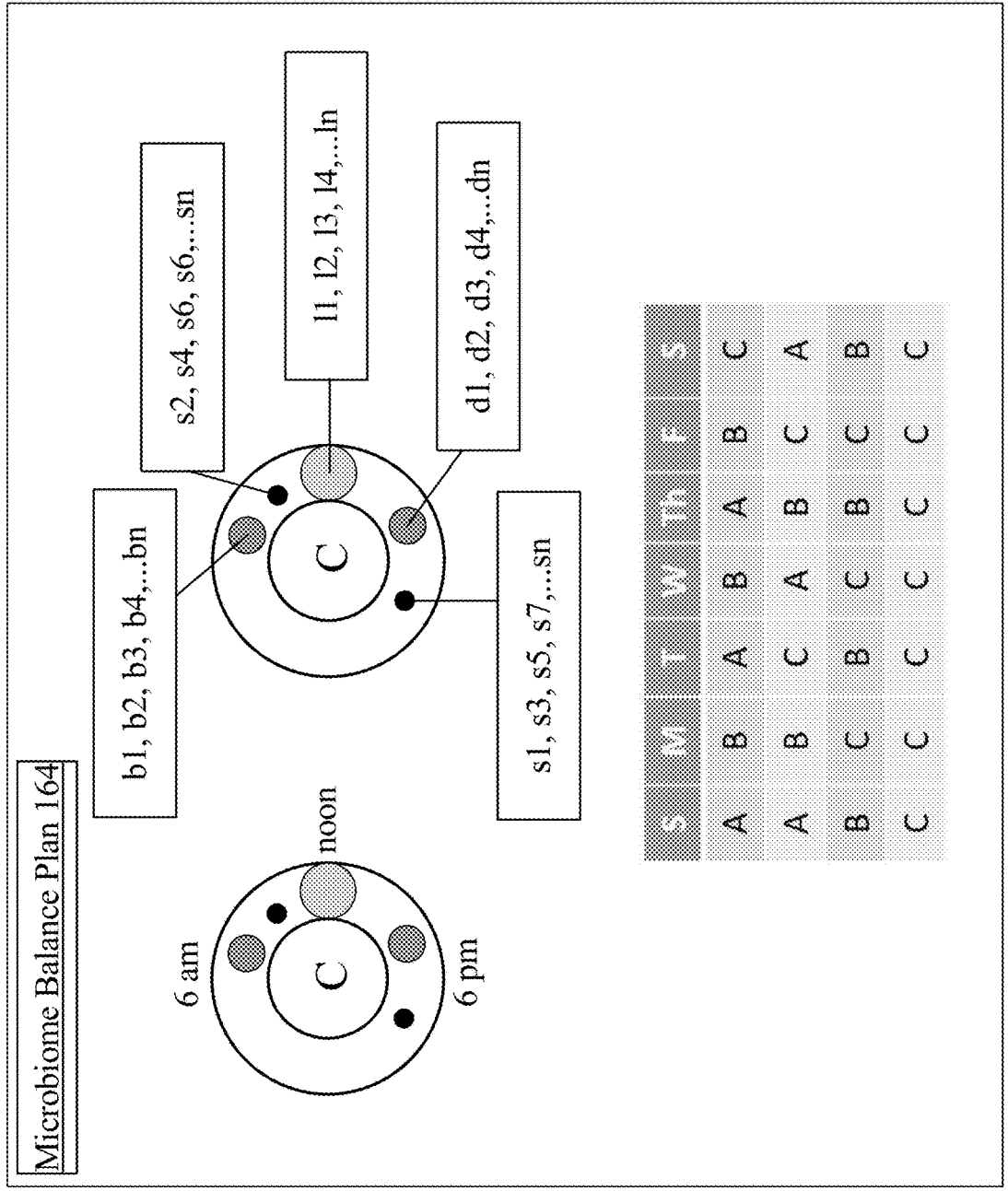
FIG. 5 is a diagrammatic representation of a microbiome balance plan.

Referring now to FIG. 5, a non-limiting exemplary embodiment 500 of microbiome balance plan 164 is illustrated. Microbiome balance plan 164 may include a schedule for arranging nutrition elements, according to for instance a 24-hour timetable, as designated on the left, where consumption is planned along a user's typical day-night cycle, beginning at ~6 am until just after 6 pm. Nutrition element may include breakfast (denoted as mid-sized dark grey circle), which may correspond to a file of breakfast-related first nutrition element 138 (denoted b1, b2, b3, b4 . . . bn, to the nth breakfast item). Nutrition element may include a first subset of snacks eaten throughout the day to, for instance supplementing beneficial organisms missing from microbiome, such as probiotics, (denoted as small black circles), which may correspond to a file of snacking-related second nutrition element 162 (denoted s2, s4, s6, s8 . . . sn, to the nth snacking item). Nutrition element may include dinner (denoted as large-sized light grey circle), which may correspond to a file of dinner-related nutrition elements (denoted d1, d2, d3, d4 . . . dn, to the nth dinner item). Microbiome balance plan 164 may include a variety of diets, as denoted in the monthly schedule at the bottom, Sunday through Saturday. Microbiome balance plan 164 'C' is shown, which may be an idealistic goal for user to achieve by the end of the month, where reduction-based plans 'A' and supplementation-based plans 'B' are intermediate plans intended to guide user to the 'balanced' microbiome. Nutrition elements classified by 'meal type' may be further modified by 'A' and 'B' according to user preferences collected by computing device 102 throughout the process. Circle sizes, denoting nutrition element classes may relate to portion sizes (magnitude), which are graphed along the circle corresponding to the timeline (frequency) they are expected to be consumed. User may indicate which nutrition element from each category was consumed, and when it was consumed, to arrive at an adherence score, as described in further detail below.

Figure 6:
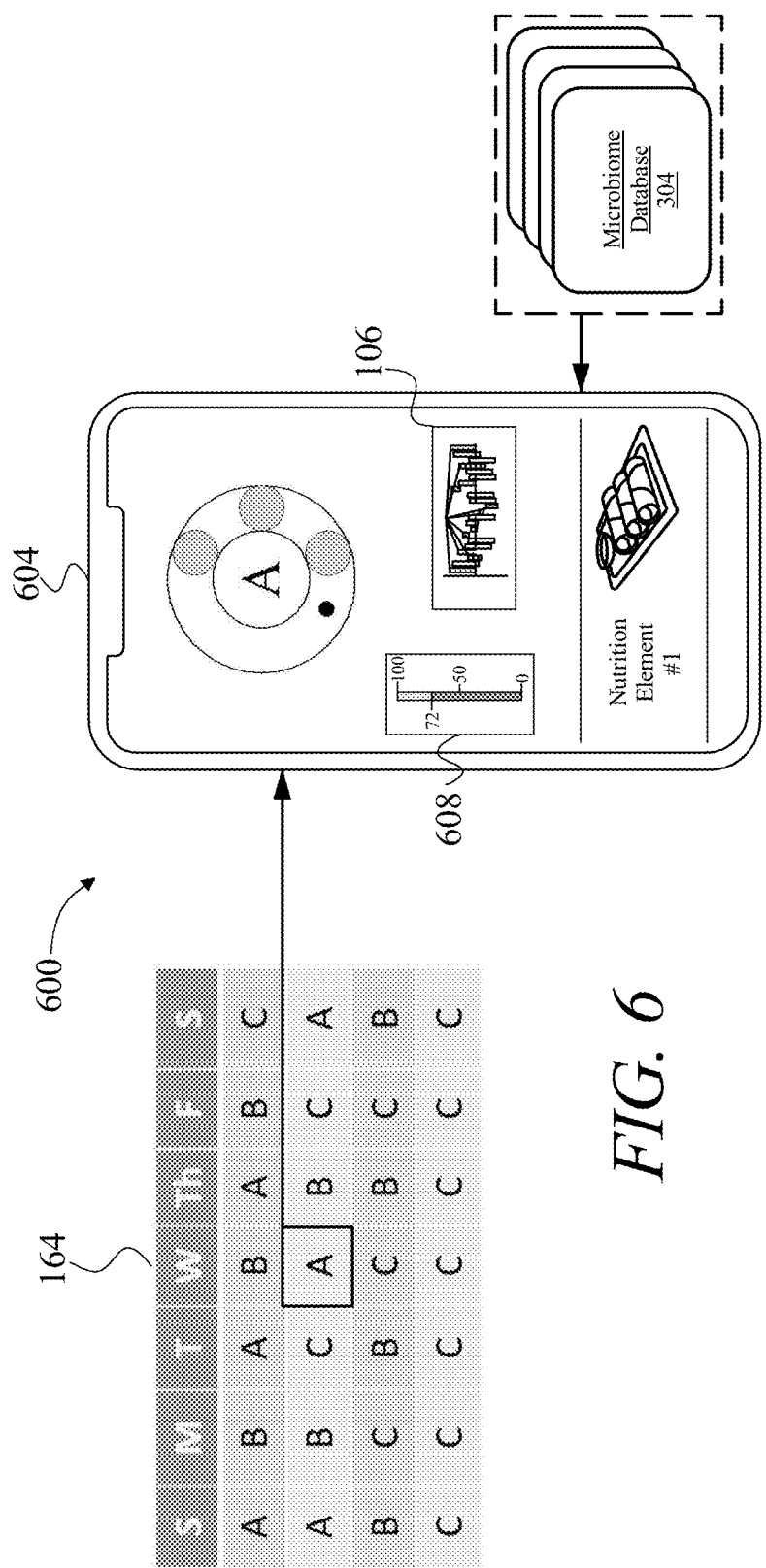
FIG. 6 is a diagrammatic representation of a user device.

Referring now to FIG. 6, a non-limiting exemplary embodiment 600 of a user device 604 is illustrated. User device 604 may include computing device 102, a "smartphone," cellular mobile phone, desktop computer, laptop, tablet computer, internet-of-things (IOT) device, wearable device, among other devices. User device 604 may include any device that is capable for communicating with computing device 102, microbiome database 304, or able to receive, transmit, and/or display, via a graphical user interface, microbiome profile 106, nutrition elements, microbiome balance plan 164, among other outputs from system 100. User device 604 may provide a "microbiome score," which as used in this disclosure, is a metric that enumerates a user's overall microbiome balance. Microbiome score 608 may increase and/or decrease with varying levels of participation and/or adherence to microbiome balance plan 164. User device 604 may provide a microbiome profile 106, for instance as a collection of parameters determined from microbe indicator 104 data. User device 604 may provide microbe category 110 that was determined as a function of microbiome profile 106. User device 604 may provide data concerning nutrient amounts, including the levels of specific nutrients, nutrient ranges, nutrients to avoid, and the like User device 604 may link timing of foods to preemptive ordering interface for ordering a nutrition element, for instance and without limitation, through a designated mobile application, mapping tool or application, and the like, and a radial search method about a user's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. User device 604 may display nutrition elements as a function of current user location. User device 604 may link microbiome balance plan 164 to a scheduling application, such as a 'calendar' feature on user device 604, which may set audio-visual notifications, timers, alarms, and the like.

Continuing in reference to FIG. 6, user device 604 may include any device that is capable for communicating with computing device 102, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Figure 7:
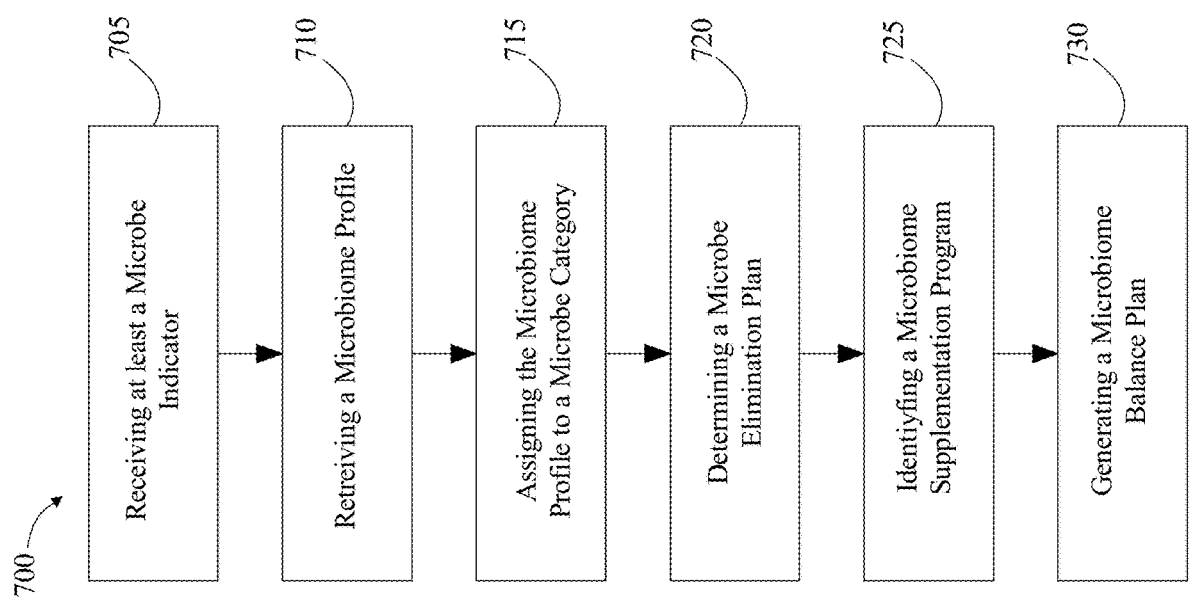
FIG. 7 is a block diagram of a workflow of a method for generating a microbiome balance plan for prevention of bacterial infection.

Referring now to FIG. 7, an exemplary embodiment 700 of a method for generating a microbiome balance plan for prevention of bacterial infection is illustrated. At step 705, the method includes receiving, by a computing device 102, at least a microbe indicator 104; this may be implemented, without limitation, as described above in FIGS. 1-6.

Still referring to FIG. 7, at step 710, method includes retrieving, by the computing device 102, a microbiome profile 106 related to the user. Retrieving the microbiome profile 106 related to the user may include training a microbiome profile machine-learning model 108 with the training data that includes a plurality of data entries wherein each entry correlates microbe indicators 104 to a plurality of microorganisms and generating the microbiome profile 106 as a function of the microbiome profile machine-learning model 108 and the at least a microbe indicator 104; this may be implemented, without limitation, as described above in FIGS. 1-6.

Continuing in reference to FIG. 7, at step 715, method includes assigning, by the computing device 102, the microbiome profile 106 to a microbe category 110, wherein the microbe category 110 is a determination about a current microbial colonization state of the user according to a classification of the user according to subsets of a plurality of users. Assigning the microbiome profile 106 to a microbe category 110 may include training a microbiome classifier 112 using a microbiome classification machine-learning process 114 and training data which includes a plurality of data entries of microbiome profile 106 data from subsets of categorized users, classifying the microbiome profile 106 to the microbe category 110 using the microbiome classifier 112, and assigning the microbe category 110 as a function of the classifying; this may be implemented, without limitation, as described above in FIGS. 1-6.

Continuing in reference to FIG. 1, at step 720, method includes determining, by the computing device 102, using the microbe category 110 and the microbiome profile 106, a microbe reduction strategy 116, wherein determining the microbe reduction strategy 116 includes locating at least a first microbe 118 to be eliminated from microbiome profile 106, identifying at least a first nutrient amount 132 that aids in reduction of the at least a first microbe 118, and determining a first nutrition element 138, wherein each nutrition element of the first nutrition element 138 contains at least a first nutrient amount 132 intended to eliminate the at least a first microbe 118. Identifying at least a first microbe 118 may include generating a pathogen index 120, wherein generating the pathogen index 120 includes training a pathogenicity machine-learning model 122 using an pathogenicity machine-learning process 124 and training data which includes a plurality of data entries of microbiome profile 106 data from subsets of users correlated to indexing values for identifying pathogenic microbes, and assigning the pathogen index 144 to each element in the microbiome profile 106 of the user according to the pathogen index 120 and the pathogenicity machine-learning model 122. Identifying at least a first microbe 118 may include generating a pathogenic microbiome standard 126, wherein generating the pathogenic microbiome standard 126 may include training a pathogenicity classifier 128 using a pathogenicity classification machine-learning process 130 and training data which includes a plurality of data entries of microbiome profile 106 data from subsets of users correlated to microbe categories 110 based on pathogenicity, determining a pathogenicity threshold from the pathogenic microbiome standard 126, comparing the microbiome profile 106 of the user to the pathogenicity threshold, and identifying the at least a first microbe 118 as a function of the comparison. Determining the at least a first nutrient amount 132 that aids in reduction of the at least a first microbe 118 may include training an reduction model 134 using an reduction machine-learning process 136 and training data, wherein training data includes a plurality of data entries of nutrition amounts correlated to reducing microbial populations and determining the at least a first nutrient amount 132 as a function of the at least a first microbe 118 and the reduction model 134; this may be implemented, without limitation, as described above in FIGS. 1-6.

Continuing in reference to FIG. 7, at step 725, method includes identifying, by the computing device 102, using the microbe category 110 and the microbiome profile 106, a microbiome supplementation program 140, wherein determining the microbiome supplementation program 140 includes locating at least a second microbe 142 to be included to the microbiome profile 106 according to the classification, determining at least a second nutrient amount 156 that aids in supplementation to microbiome profile 106 of the at least a second microbe 142, and identifying a second nutrition element 162, wherein each nutrition element of the second nutrition element 162 contains at least a second nutrient amount 156 intended to supplement the at least a second microbe 142. Identifying at least a second microbe 142 may include generating a balancing index 144, wherein generating the balancing index 144 includes training a microbe balancing machine-learning model 146 using a microbe balancing machine-learning process 148 and training data which includes a plurality of data entries of microbiome profile 106 data from subsets of users correlated to indexing values for identifying beneficial microbes, and assigning the balancing index 144 to each element in the microbiome profile 106 of the user according to the balancing index 144 and the microbe balancing machine-learning model 146. Identifying at least a second microbe 142 may include generating a balancing standard 150, wherein generating the balancing standard 150 may include training a microbe balancing classifier 152 using a balancing classification machine-learning process 154 and training data which includes a plurality of data entries of microbiome profile 106 data from subsets of users correlated to microbe categories 110 based on incidence of microbes, determining a balancing threshold from the balancing standard 150, comparing the microbiome profile 106 of the user to the balancing standard 150, and identifying the at least a second microbe 142 as a function of the comparison. Determining the at least a second nutrient amount 156 that aids in supplementation of the at least a second microbe 142 may include training a supplementation model 158 using a supplementation machine-learning process 160 and training data, wherein training data includes a plurality of data entries of nutrition amounts correlated to increasing microbial populations, and determining the at least a second nutrient amount 156 as a function of the at least a second microbe 142 and the supplementation model 158; this may be implemented, without limitation, as described above in FIGS. 1-6.

Continuing in reference to FIG. 7, at step 730, method includes generating, by the computing device, a microbiome balance plan 164, using the microbe reduction strategy 116 and the microbiome supplementation program 140, wherein the microbiome balance plan 164 includes a frequency and a magnitude for establishing balanced colonization in the user. Generating the microbiome balance plan 164 may include generating an objective function with the at least a first nutrition element 132 and the at least a second nutrition element 162 wherein the objection function outputs at least an ordering of a plurality of nutrition elements according to constraints from the microbe reduction strategy 116 and the microbiome supplementation program 140; this may be implemented, without limitation, as described above in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
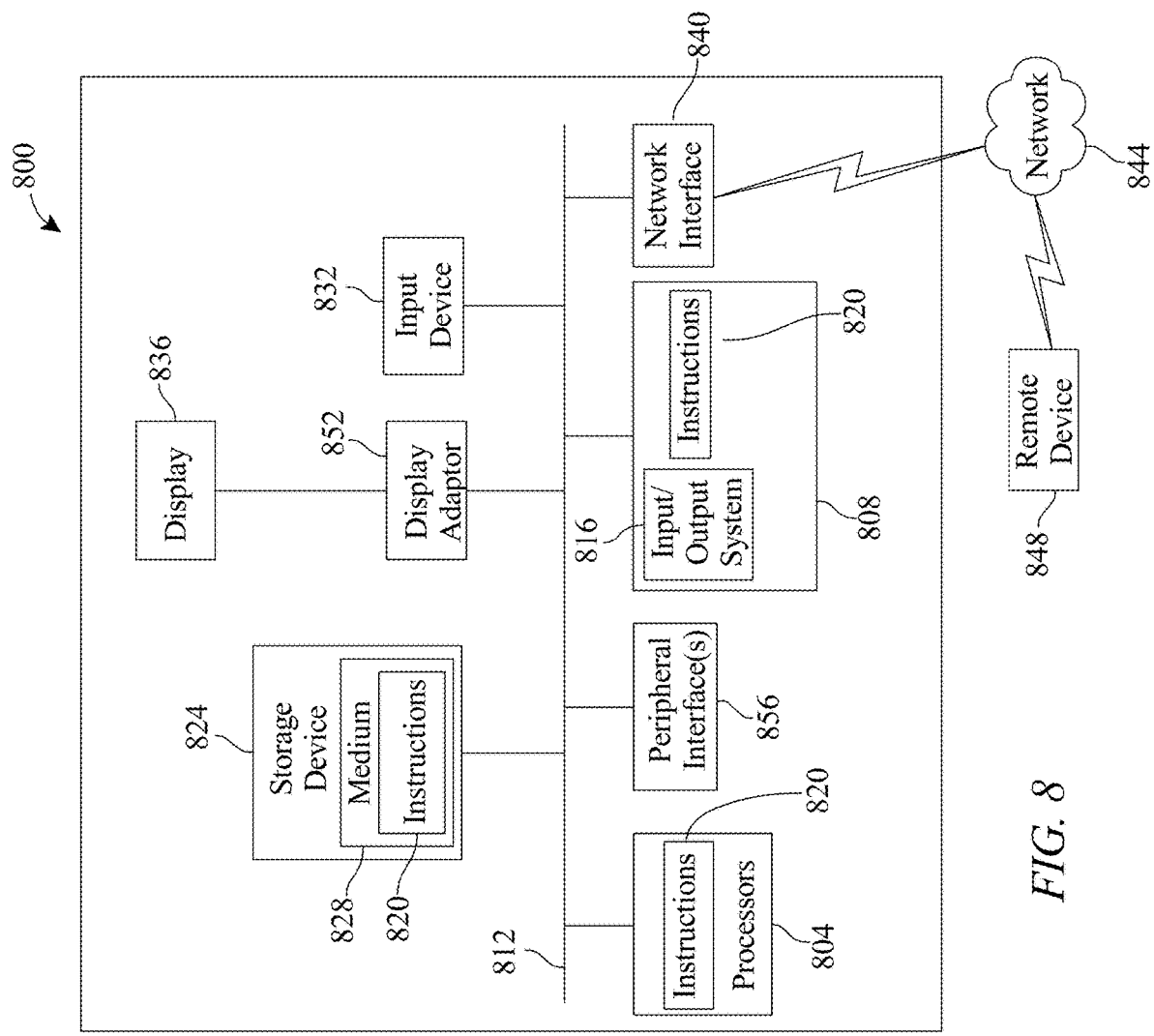
FIG. 8 is a block diagram of a computing system that can be used to implement any one or more of the methodologies disclosed herein and any one or more portions thereof.

Referring now to FIG. 8, a diagrammatic representation of one embodiment of a computing device in the exemplary form of a computer system 800 within which a set of instructions for causing a control system to perform any one or more of the aspects and/or methodologies of the present disclosure may be executed is illustrated. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Continuing in reference to FIG. 8, processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Continuing in reference to FIG. 8, memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Continuing in reference to FIG. 8, computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Continuing in reference to FIG. 8, computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

Continuing in reference to FIG. 8, a user may also input commands and/or other information to computer system 800 via storage device 824 (e.g., a removable disk drive, a flash drive, and the like) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, and the like) may be communicated to and/or from computer system 800 via network interface device 840.

Continuing in reference to FIG. 8, computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a microbiome balance plan for prevention of bacterial infection, the system comprising a computing device, wherein the computing device is configured to:
   receive at least a microbe indicator, wherein a microbe indicator is a biomarker that originates from a user;
   retrieve a microbiome profile related to the user, wherein retrieving the microbiome profile further comprises:
      training a microbiome profile machine-learning model with training data wherein the training data includes a plurality of data entries correlating a plurality of microbe indicators to a plurality of microorganisms; and
      generating the microbiome profile as a function of the training data and the microbiome profile machine-learning model;
   assign the microbiome profile to a microbe category;
   determine, using the microbe category and the microbiome profile, a microbe reduction strategy, wherein determining the microbe reduction strategy includes:
      locating at least a first microbe to be reduced from the microbiome profile;
      identifying at least a first nutrient amount that aids in reduction of the at least a first microbe; and
      determining at least a first nutrition element, wherein the at least a first nutrition element includes the at least a first nutrient;
   identify, using the microbe category and the microbiome profile, a microbiome supplementation program, wherein determining the microbiome supplementation program includes:
      locating at least a second microbe to be included to the microbiome profile;
      determining at least a second nutrient amount that aids in supplementation to microbiome profile of the at least a second microbe; and
      identifying at least a second nutrition element, wherein of the at least a second nutrition element includes the at least a second nutrient amount; and
   generate a microbiome balance plan, using the microbe reduction strategy and the microbiome supplementation program, wherein the microbiome balance plan includes a frequency of the at least a first nutrient element, a magnitude of the at least a first nutrient element, a frequency of the at least a second nutrient element, and a magnitude of the at least a second nutrient element; and
   display the microbiome balance plan to the user.

2. The system of claim 1, wherein assigning the microbiome profile to a microbe category further comprises:
   training a microbiome classifier using a microbiome classification machine-learning process and training data including a plurality of data entries correlating microbiome profile data to subsets of categorized users;
   classifying the microbiome profile to the microbe category using the microbiome classifier; and
   assigning the microbe category as a function of the classifying.

3. The system of claim 1, wherein identifying the at least a first microbe further comprises generating a pathogen index, wherein generating the pathogen index includes:
   training a pathogenicity machine-learning model using a pathogenicity machine-learning process and training data including a plurality of data entries of microbiome profile data from subsets of users correlated to indexing values for identifying pathogenic microbes; and assigning the pathogen index to each element in the microbiome profile of the user according to the pathogen index and the pathogenicity machine-learning model.

4. The system of claim 3, wherein identifying the at least a first microbe further comprises:

generating a pathogenic microbiome standard, wherein generating the pathogenic microbiome standard further comprises training a pathogenicity classifier using a pathogenicity classification machine-learning process and training data including a plurality of data entries of microbiome profile data from subsets of users correlated to microbe categories based on pathogenicity;

determining a pathogenicity threshold from the pathogenic microbiome standard;

comparing the microbiome profile of the user to the pathogenicity threshold; and identifying the at least a first microbe as a function of the comparison.

5. The system of 1, determining the at least a first nutrient amount that aids in reduction of the at least a first microbe further comprises:

training a reduction model using a reduction machine-learning process and training data, wherein training data includes a plurality of data entries of nutrition amounts correlated to reducing microbial populations; and determining the at least a first nutrient amount as a function of the at least a first microbe and the reduction model.

6. The system of claim 1, wherein identifying at least a second microbe further comprises generating a balancing index, wherein generating the balancing index includes:

training a microbe balancing machine-learning model using a microbe balancing machine-learning process and training data including a plurality of data entries of microbiome profile data from subsets of users correlated to indexing values for identifying beneficial microbes; and assigning the balancing index to each element in the microbiome profile of the user according to the balancing index and the microbe balancing machine-learning model.

7. The system of claim 6, wherein identifying the at least a second microbe further comprises:

generating a balancing standard, wherein generating the balancing standard further comprises training a microbe balancing classifier using a balancing classification machine-learning process and training data which includes a plurality of data entries of microbiome profile data from subsets of users correlated to microbe categories based on incidence of microbes;

determining a balancing threshold from the balancing standard;

comparing the microbiome profile of the user to the balancing standard; and identifying the at least a second microbe as a function of the comparison.

8. The system of 1, determining the at least a second nutrient amount that aids in supplementation of the at least a second microbe further comprises:

training a supplementation model using a supplementation machine-learning process and training data, wherein training data includes a plurality of data entries of nutrition amounts correlated to increasing microbial populations; and determining the at least a second nutrient amount as a function of the at least a second microbe and the supplementation model.

9. The system of claim 1, wherein generating the microbiome balance plan further comprises generating an objective function with the at least a first nutrition element and the at least a second nutrition element wherein the objection function outputs at least an ordering of a nutrition element according to constraints from the microbe reduction strategy and the microbiome supplementation program.

10. A method for generating a microbiome balance plan for prevention of bacterial infection, the method comprising:

receiving, by a computing device, at least a microbe indicator, wherein a microbe indicator is a biomarker that originates from a user;

retrieving, by the computing device, a microbiome profile related to the user, wherein retrieving the microbiome profile further comprises:

training a microbiome profile machine-learning model with training data wherein the training data includes a plurality of data entries correlating a plurality of microbe indicators to a plurality of microorganisms; and generating the microbiome profile as a function of the training data and the microbiome profile machine-learning model;

assigning, by the computing device, the microbiome profile to a microbe category;

determining, by the computing device, using the microbe category and the microbiome profile, a microbe reduction strategy, wherein determining the microbe reduction strategy includes:

locating at least a first microbe to be reduced from the microbiome profile;

identifying at least a first nutrient amount that aids in reduction of the at least a first microbe; and determining at least a first nutrition element, wherein the at least a first nutrition element includes the at least a first nutrient;

identifying, by the computing device, using the microbe category and the microbiome profile, a microbiome supplementation program, wherein determining the microbiome supplementation program includes:

locating at least a second microbe to be included to the microbiome profile;

determining at least a second nutrient amount that aids in supplementation to microbiome profile of the at least a second microbe; and identifying at least a second nutrition element, wherein of the at least a second nutrition element includes the at least a second nutrient amount; and generating, by the computing device, a microbiome balance plan, using the microbe reduction strategy, and the microbiome supplementation program, wherein the microbiome balance plan includes a frequency and a magnitude of the at least a first nutrient element, and a frequency and a magnitude of the at least a second nutrient element; and displaying, by the computing device, the microbiome balance plan to the user.

11. The method of claim 10, wherein assigning the microbiome profile to a microbe category further comprises:

training a microbiome classifier using a microbiome classification machine-learning process and training data including a plurality of data entries correlating microbiome profile data to subsets of categorized users;
classifying the microbiome profile to the microbe category using the microbe classifier; and
assigning the microbe category as a function of the classifying.

12. The method of claim 10, wherein identifying the at least a first microbe further comprises generating a pathogen index, wherein generating the pathogen index includes:
training a pathogenicity machine-learning model using a pathogenicity machine-learning process and training data including a plurality of data entries of microbiome profile data from subsets of users correlated to indexing values for identifying pathogenic microbes; and
assigning the pathogen index to each element in the microbiome profile of the user according to the pathogen index and the pathogenicity machine-learning model.

13. The method of claim 12, wherein identifying the at least a first microbe further comprises:
generating a pathogenic microbiome standard, wherein generating the pathogenic microbiome standard further comprises training a pathogenicity classifier using a pathogenicity classification machine-learning process and training data including a plurality of data entries of microbiome profile data from subsets of users correlated to microbe categories based on pathogenicity;
determining a pathogenicity threshold from the pathogenic microbiome standard;
comparing the microbiome profile of the user to the pathogenicity threshold; and
identifying the at least a first microbe as a function of the comparison.

14. The method of 10, determining the at least a first nutrient amount that aids in reduction of the at least a first microbe further comprises:
training a reduction model using a reduction machine-learning process and training data, wherein training data includes a plurality of data entries of nutrition amounts correlated to reducing microbial populations; and
determining the at least a first nutrient amount as a function of the at least a first microbe and the reduction model.

15. The method of claim 10, wherein identifying at least a second microbe further comprises generating a balancing index, wherein generating the balancing index includes:
training a microbe balancing machine-learning model using a microbe balancing machine-learning process and training data including a plurality of data entries of microbiome profile data from subsets of users correlated to indexing values for identifying beneficial microbes; and
assigning the balancing index to each element in the microbiome profile of the user according to the balancing index and the microbe balancing machine-learning model.

16. The method of claim 15, wherein identifying the at least a second microbe further comprises:
generating a balancing standard, wherein generating the balancing standard further comprises training a microbe balancing classifier using a balancing classification machine-learning process and training data which includes a plurality of data entries of microbiome profile data from subsets of users correlated to microbe categories based on incidence of microbes;
determining a balancing threshold from the balancing standard;
comparing the microbiome profile of the user to the balancing standard; and
identifying the at least a second microbe as a function of the comparison.

17. The method of 10, determining the at least a second nutrient amount that aids in supplementation of the at least a second microbe further comprises:
training a supplementation model using a supplementation machine-learning process and training data, wherein training data includes a plurality of data entries of nutrition amounts correlated to increasing microbial populations; and
determining the at least a second nutrient amount as a function of the at least a second microbe and the supplementation model.

18. The method of claim 10, wherein generating the microbiome balance plan further comprises generating an objective function with the at least a first nutrition element and the at least a second nutrition element wherein the objection function outputs at least an ordering of a nutrition element according to constraints from the microbe reduction strategy and the microbiome supplementation program.

* * * * *